(12) United States Patent
Casebier

(10) Patent No.: US 9,359,395 B2
(45) Date of Patent: Jun. 7, 2016

(54) PRODRUGS OF STEROIDAL CYP17 INHIBITORS/ANTIANDROGENS

(71) Applicant: Tokai Pharmaceuticals, Inc., Cambridge, MA (US)

(72) Inventor: David S. Casebier, Carlisle, MA (US)

(73) Assignee: Tokai Pharmaceuticals, Inc., Boston, MA (US)

( * ) Notice: Subject to any disclaimer, the term of this patent is extended or adjusted under 35 U.S.C. 154(b) by 0 days.

(21) Appl. No.: 14/328,378

(22) Filed: Jul. 10, 2014

(65) Prior Publication Data

US 2014/0371181 A1    Dec. 18, 2014

Related U.S. Application Data

(63) Continuation of application No. 13/146,004, filed as application No. PCT/US2010/023391 on Feb. 5, 2010, now abandoned.

(60) Provisional application No. 61/150,031, filed on Feb. 5, 2009.

(51) Int. Cl.
| | |
|---|---|
| *C07J 43/00* | (2006.01) |
| *A61K 31/58* | (2006.01) |
| *A61K 31/675* | (2006.01) |
| *A61K 45/06* | (2006.01) |
| *A61N 5/10* | (2006.01) |

(52) U.S. Cl.
CPC ............... *C07J 43/003* (2013.01); *A61K 31/58* (2013.01); *A61K 31/675* (2013.01); *A61K 45/06* (2013.01); *A61N 5/10* (2013.01)

(58) Field of Classification Search
CPC ..... C07J 43/003; A61K 31/58; A61K 31/675; A61K 45/06; A61N 5/10; C07D 235/04
USPC .......................................... 540/95; 548/304.4
See application file for complete search history.

(56) References Cited

U.S. PATENT DOCUMENTS

| | | | |
|---|---|---|---|
| 2,664,423 A | 12/1953 | Rorig | |
| 3,060,174 A | 10/1962 | Albert et al. | |
| 3,313,809 A | 4/1967 | Clinton et al. | |
| 3,317,520 A | 5/1967 | Clinton | |
| 3,480,621 A | 11/1969 | Loken et al. | |
| 3,539,687 A | 11/1970 | Kuhnen et al. | |
| 4,000,125 A | 12/1976 | Casagrande et al. | |
| 4,316,885 A | 2/1982 | Rakhit | |
| 4,650,803 A | 3/1987 | Stella et al. | |
| 5,023,263 A | 6/1991 | Von Burg | |
| 5,023,264 A | 6/1991 | Caufield et al. | |
| 5,028,726 A | 7/1991 | Farrell | |
| 5,100,883 A | 3/1992 | Schiehser | |
| 5,104,895 A | 4/1992 | Spinelli et al. | |
| 5,118,677 A | 6/1992 | Caufield | |
| 5,118,678 A | 6/1992 | Kao et al. | |
| 5,120,842 A | 6/1992 | Failli et al. | |
| 5,151,413 A | 9/1992 | Caufield et al. | |
| 5,162,333 A | 11/1992 | Failli et al. | |
| 5,177,203 A | 1/1993 | Failli et al. | |
| 5,221,670 A | 6/1993 | Caufield | |
| 5,232,917 A | 8/1993 | Bolger et al. | |
| 5,233,036 A | 8/1993 | Hughes | |
| 5,237,064 A | 8/1993 | Bakshi et al. | |
| 5,256,790 A | 10/1993 | Nelson | |
| 5,258,389 A | 11/1993 | Goulet et al. | |
| 5,260,300 A | 11/1993 | Hu | |
| 5,262,423 A | 11/1993 | Kao | |
| 5,264,427 A | 11/1993 | Brodie et al. | |
| 5,270,163 A | 12/1993 | Gold et al. | |
| 5,300,294 A | 4/1994 | Johnson | |
| 5,302,584 A | 4/1994 | Kao et al. | |
| 5,362,718 A | 11/1994 | Skotnicki et al. | |
| 5,373,014 A | 12/1994 | Failli et al. | |
| 5,378,836 A | 1/1995 | Kao et al. | |
| 5,385,908 A | 1/1995 | Nelson et al. | |
| 5,385,909 A | 1/1995 | Nelson et al. | |
| 5,385,910 A | 1/1995 | Ocain et al. | |
| 5,385,936 A | 1/1995 | Flack et al. | |

(Continued)

FOREIGN PATENT DOCUMENTS

| | | |
|---|---|---|
| CN | 101023349 A | 8/2007 |
| CN | 101607985 A | 12/2009 |

(Continued)

OTHER PUBLICATIONS

Abstract ANIH Grant Project Reference No. 5RO1 CA27440-24, approximate date Feb. 20, 2003; approximate award date Jun. 3, 2003.
Abstract of NIH Grant Project Reference No. 2R01 CA27440-25A1, approximate submission date Feb. 18, 2004; approximate award date Sep. 23, 2004.
Abstract of NIH Grant Project Reference No. 3RO1 CA27440-22S1, approximate date Jun. 21, 2001; approximate award date Aug. 17, 2001.
Abstract of NIH Grant Project Reference No. 3RO1 CA27440-23S1, approximate date May 3, 2002; approximate award date Jun. 21, 2002.
Abstract of NIH Grant Project Reference No. 5RO1 CA27440-23, approximate date Jan. 21, 2002; approximate award date Apr. 29, 2002.

(Continued)

*Primary Examiner* — T. Victor Oh
(74) *Attorney, Agent, or Firm* — Choate, Hall & Stewart LLP; Brenda Herschbach Jarrell; Michael A. Shinall

(57) ABSTRACT

Prodrugs of C-17-heterocyclic-steroidal drugs providing improved oral bioavailability and phamacokinetics are described. The drugs are inhibitors of human CYP 17 enzyme, as well as potent antagonists of both wild type and mutant androgen receptors (AR), and are useful for the treatment of urogenital and/or androgen-related cancers, diseases and/or conditions, such as human prostate cancer, breast cancer, and prostate hyperplasia. The disclosure describes methods of synthesizing and using the prodrugs in cancer therapy.

9 Claims, No Drawings

(56) References Cited

U.S. PATENT DOCUMENTS

| | | |
|---|---|---|
| 5,389,639 A | 2/1995 | Failli et al. |
| 5,391,730 A | 2/1995 | Skotnicki et al. |
| 5,411,967 A | 5/1995 | Kao et al. |
| 5,434,260 A | 7/1995 | Skotnicki et al. |
| 5,456,923 A | 10/1995 | Nakamichi et al. |
| 5,463,048 A | 10/1995 | Skotnicki et al. |
| 5,475,096 A | 12/1995 | Gold et al. |
| 5,480,988 A | 1/1996 | Failli et al. |
| 5,480,989 A | 1/1996 | Kao et al. |
| 5,489,680 A | 2/1996 | Failli et al. |
| 5,491,231 A | 2/1996 | Nelson et al. |
| 5,496,556 A | 3/1996 | Johnson |
| 5,504,091 A | 4/1996 | Molnar-Kimber et al. |
| 5,512,570 A | 4/1996 | Dorn et al. |
| 5,563,145 A | 10/1996 | Failli et al. |
| 5,567,588 A | 10/1996 | Gold et al. |
| 5,595,877 A | 1/1997 | Gold et al. |
| 5,601,981 A | 2/1997 | Malins |
| 5,604,213 A | 2/1997 | Barrie et al. |
| 5,620,986 A | 4/1997 | Witzel et al. |
| 5,637,310 A | 6/1997 | Johnson |
| 5,637,459 A | 6/1997 | Burke et al. |
| 5,660,985 A | 8/1997 | Pieken et al. |
| 5,665,772 A | 9/1997 | Cottens et al. |
| 5,670,637 A | 9/1997 | Gold et al. |
| 5,672,605 A | 9/1997 | Or et al. |
| 5,683,867 A | 11/1997 | Biesecker et al. |
| 5,696,249 A | 12/1997 | Gold et al. |
| 5,707,796 A | 1/1998 | Gold et al. |
| 5,721,227 A | 2/1998 | Melloni et al. |
| 5,741,795 A | 4/1998 | Aster et al. |
| 5,780,462 A | 7/1998 | Lee et al. |
| 5,994,334 A | 11/1999 | Brodie et al. |
| 5,994,335 A | 11/1999 | Brodie et al. |
| 6,011,020 A | 1/2000 | Gold et al. |
| 6,133,280 A | 10/2000 | Brodie et al. |
| 6,200,965 B1 | 3/2001 | Brodie et al. |
| 6,368,598 B1 | 4/2002 | D'Amico et al. |
| 6,444,649 B1 | 9/2002 | Inamori et al. |
| 6,444,683 B2 | 9/2002 | Brodie et al. |
| 6,548,555 B1 | 4/2003 | Curatolo et al. |
| 6,763,607 B2 | 7/2004 | Beyerinck et al. |
| 6,933,312 B2 | 8/2005 | Price et al. |
| 6,960,584 B2 | 11/2005 | Carling et al. |
| 6,973,741 B2 | 12/2005 | Beyerinck et al. |
| 6,982,258 B2 | 1/2006 | Posner et al. |
| 7,098,208 B2 | 8/2006 | Owens et al. |
| 7,192,974 B2 | 3/2007 | Gravestock et al. |
| 7,223,738 B2 | 5/2007 | Bilodeau et al. |
| 7,304,063 B2 | 12/2007 | Bilodeau et al. |
| 7,378,403 B2 | 5/2008 | Kozikowski et al. |
| 7,396,832 B2 | 7/2008 | Lindsley et al. |
| 7,399,764 B2 | 7/2008 | Duggan et al. |
| 7,414,055 B2 | 8/2008 | Duggan et al. |
| 7,544,677 B2 | 6/2009 | Bilodeau et al. |
| 7,576,209 B2 | 8/2009 | Kelly et al. |
| 7,579,355 B2 | 8/2009 | Bilodeau et al. |
| 7,589,068 B2 | 9/2009 | Cosford et al. |
| 7,604,947 B2 | 10/2009 | Gudas |
| 7,638,530 B2 | 12/2009 | Bilodeau et al. |
| 7,655,649 B2 | 2/2010 | Bilodeau et al. |
| 7,705,014 B2 | 4/2010 | Chen et al. |
| 7,750,151 B2 | 7/2010 | Bilodeau et al. |
| 7,780,988 B2 | 8/2010 | Beyerinck et al. |
| 7,807,393 B2 | 10/2010 | Thaxton et al. |
| 7,875,599 B2 | 1/2011 | Brodie |
| 7,887,840 B2 | 2/2011 | Curatolo et al. |
| 7,943,732 B2 | 5/2011 | Reed |
| 7,960,435 B2 | 6/2011 | Njar et al. |
| 8,003,643 B2 | 8/2011 | Bilodeau et al. |
| 8,003,651 B2 | 8/2011 | Mitchell et al. |
| 8,008,317 B2 | 8/2011 | Armstrong et al. |
| 8,026,286 B2 | 9/2011 | Curatolo et al. |
| 8,110,550 B2 | 2/2012 | Brodie et al. |
| 8,129,184 B2 | 3/2012 | Yu |
| 8,133,724 B2 | 3/2012 | Qiu et al. |
| 8,168,652 B2 | 5/2012 | Sanderson et al. |
| 8,263,357 B2 | 9/2012 | Reed |
| 8,273,782 B2 | 9/2012 | Seefeld et al. |
| 8,324,221 B2 | 12/2012 | Banka et al. |
| 8,785,423 B2 | 7/2014 | Njar et al. |
| 8,791,094 B2 | 7/2014 | Morrison et al. |
| 8,791,095 B2 | 7/2014 | Casebier |
| 8,822,438 B2 | 9/2014 | Auerbach et al. |
| 8,841,422 B2 | 9/2014 | Qiu et al. |
| 9,018,198 B2 | 4/2015 | Njar et al. |
| 9,156,878 B2 | 10/2015 | Morrison et al. |
| 2001/0001099 A1 | 5/2001 | Brodie et al. |
| 2002/0009494 A1 | 1/2002 | Curatolo et al. |
| 2003/0054053 A1 | 3/2003 | Young et al. |
| 2003/0059471 A1 | 3/2003 | Compton et al. |
| 2004/0058896 A1 | 3/2004 | Dietrich et al. |
| 2006/0013873 A1 | 1/2006 | Yang et al. |
| 2007/0037887 A1 | 2/2007 | Santen et al. |
| 2007/0185152 A1 | 8/2007 | Yamashita et al. |
| 2007/0238647 A1 | 10/2007 | Bowen et al. |
| 2008/0058301 A1 | 3/2008 | Lardy et al. |
| 2008/0280864 A1 | 11/2008 | Brodie et al. |
| 2009/0012045 A1 | 1/2009 | Hitoshi et al. |
| 2009/0047252 A1 | 2/2009 | Cai et al. |
| 2009/0048149 A1 | 2/2009 | Ng et al. |
| 2009/0221672 A1 | 9/2009 | Zhang et al. |
| 2010/0009397 A1 | 1/2010 | Sebti et al. |
| 2010/0029667 A1 | 2/2010 | Ketner et al. |
| 2010/0047338 A1 | 2/2010 | Brodie et al. |
| 2010/0048524 A1 | 2/2010 | Brodie et al. |
| 2010/0048912 A1 | 2/2010 | Brodie et al. |
| 2010/0048913 A1 | 2/2010 | Brodie et al. |
| 2010/0048914 A1 | 2/2010 | Brodie et al. |
| 2010/0068802 A1 | 3/2010 | Qiu et al. |
| 2010/0137269 A1 | 6/2010 | Brodie et al. |
| 2010/0298383 A1 | 11/2010 | Ng et al. |
| 2011/0034428 A1 | 2/2011 | Morrison et al. |
| 2011/0105445 A1 | 5/2011 | Njar et al. |
| 2011/0110926 A1 | 5/2011 | Luo et al. |
| 2011/0118219 A1 | 5/2011 | Njar et al. |
| 2011/0160170 A1 | 6/2011 | Njar et al. |
| 2011/0178070 A1 | 7/2011 | Gong et al. |
| 2011/0195966 A1 | 8/2011 | Garcia-Echeverria et al. |
| 2011/0224223 A1 | 9/2011 | Shokat et al. |
| 2011/0312916 A1 | 12/2011 | Casebier |
| 2011/0312924 A1 | 12/2011 | Casebier |
| 2011/0313229 A1 | 12/2011 | Sugaya et al. |
| 2011/0319369 A1 | 12/2011 | Casebier et al. |
| 2012/0028972 A1 | 2/2012 | Wong et al. |
| 2012/0282331 A1 | 11/2012 | Chappel et al. |
| 2013/0130241 A1 | 5/2013 | Dehm |
| 2014/0288036 A1 | 9/2014 | Brodie et al. |
| 2014/0288037 A1 | 9/2014 | Casebier et al. |
| 2014/0343024 A1 | 11/2014 | Morrison et al. |
| 2014/0371181 A1 | 12/2014 | Casebier |
| 2015/0005265 A1 | 1/2015 | Stewart |
| 2015/0051179 A1 | 2/2015 | Casebier |
| 2015/0166599 A1 | 6/2015 | Morrison et al. |
| 2015/0174143 A1 | 6/2015 | Njar et al. |
| 2015/0203528 A1 | 7/2015 | Morrison et al. |
| 2015/0297615 A1 | 10/2015 | Njar et al. |
| 2015/0320770 A1 | 11/2015 | Casebier et al. |

FOREIGN PATENT DOCUMENTS

| | | |
|---|---|---|
| EP | 0469548 A2 | 2/1992 |
| EP | 1712222 A2 | 10/2006 |
| EP | 0901786 B1 | 6/2007 |
| EP | 1530457 B1 | 9/2009 |
| GB | 972672 | 10/1964 |
| GB | 2479337 A | 10/2011 |
| JP | 38-022578 | 10/1963 |
| JP | S51-41372 | 4/1976 |
| JP | 56003000 | 1/1981 |
| JP | H06-192287 A | 7/1994 |
| JP | H07-505377 A | 6/1995 |
| JP | H08-509617 A | 10/1996 |
| JP | 2002-517433 A | 6/2002 |

(56) References Cited

FOREIGN PATENT DOCUMENTS

| | | |
|---|---|---|
| JP | 2008-536807 A | 9/2008 |
| WO | WO-92/05179 A1 | 4/1992 |
| WO | WO-93/11130 A1 | 6/1993 |
| WO | WO 93/20097 A1 | 10/1993 |
| WO | WO-94/02136 A1 | 2/1994 |
| WO | WO-94/02485 A1 | 2/1994 |
| WO | WO-94/09010 A1 | 4/1994 |
| WO | WO-94/25626 A1 | 11/1994 |
| WO | WO-95/14023 A1 | 5/1995 |
| WO | WO-95/16691 A1 | 6/1995 |
| WO | WO-96/41807 A1 | 12/1996 |
| WO | WO-98/02441 A2 | 1/1998 |
| WO | WO 99/63974 A2 | 12/1999 |
| WO | WO-01/14387 A1 | 3/2001 |
| WO | WO-01/19828 A2 | 3/2001 |
| WO | WO-03/032950 A1 | 4/2003 |
| WO | WO 2005/009429 A1 | 2/2005 |
| WO | WO 2005/014023 A1 | 2/2005 |
| WO | WO-2005/047289 A1 | 5/2005 |
| WO | WO-2005/097107 A2 | 10/2005 |
| WO | WO 2006/093993 A1 | 9/2006 |
| WO | WO-2007/061737 A2 | 5/2007 |
| WO | WO-2007/064993 A2 | 6/2007 |
| WO | WO-2007/087395 A2 | 8/2007 |
| WO | WO-2008/027855 A2 | 3/2008 |
| WO | WO-2008/109163 A1 | 9/2008 |
| WO | WO-2008/154382 A1 | 12/2008 |
| WO | WO-2009/114658 A2 | 9/2009 |
| WO | WO 2009/120565 A2 | 10/2009 |
| WO | WO 2009/120565 A3 | 3/2010 |
| WO | WO-2010/028646 A1 | 3/2010 |
| WO | WO-2010/089763 A2 | 8/2010 |
| WO | WO-2010/091299 A2 | 8/2010 |
| WO | WO-2010/091306 A1 | 8/2010 |
| WO | WO-2010/111132 A2 | 9/2010 |
| WO | WO-2011/116343 A2 | 9/2011 |
| WO | WO-2012/129408 A2 | 9/2012 |
| WO | WO-2013/079964 A1 | 6/2013 |
| WO | WO-2013/096907 A1 | 6/2013 |

OTHER PUBLICATIONS

Abstract of NIH Grant Project Reference No. 5RO1 CA27440-24S1, approximate date Apr. 1, 2003; approximate award date Jun. 3, 2003.

Abstract of NIH Grant Project Reference No. 5RO1 CA27440-26, approximate submission date Jul. 1, 2005; approximate award date Aug. 2, 2005.

Abstract of NIH Grant Project Reference No. 5RO1CA27440-27, approximate submission date Apr. 26, 2006.

Barrie, et al. Pharmacology of novel steroidal inhibitors of cytochrome P450(17) alpha (17 alpha-hydroxylase/C17-20 lyase). J Steroid Biochem Mol Biol. Sep. 1994;50(5-6):267-73.

Bruchovsky, et al. The conversion of testosterone to 5-alpha-androstan-17-beta-ol-3-one by rat prostate in vivo and in vitro. J Biol Chem. Apr. 25, 1968;243(8):2012-21.

Chen, et al. Molecular determinants of resistance to antiandrogen therapy. Nat Med. Jan. 2004;10(1):33-9.

Chengjie, et al. Synthesis of pharmacological activity of some 17-[(2'-substituted)-4'-pyramidyl] androstene derivatives as inhibitors of human 17alpha-hydroxylase/C17,20-layse. J. Chinese Pharm. Sci. 2001; 10(1):3-8.

Choshi, et al. Total synthesis of grossularines-1 and -2. J. Org. Chem. 1995; 60:5899-5904.

Clement, et al. Three dimensional pharmacophore modeling of human CYP17 inhibitors. Potential agents for prostate cancer therapy. J Med Chem. Jun. 5, 2003;46(12):2345-51.

Crawford, et al. A controlled trial of leuprolide with and without flutamide in prostatic carcinoma. New Eng J Med. 1989; 321:419-424.

Crawford, et al. Treatment of newly diagnosed stage D2 prostate cancer with leuprolide and flutamide or leuprolide alone, phase III: prognostic significance of minimal disease. J. Urol. 1992; 147:417A.

Denis. Role of maximal androgen bloackade in advanced prostate cancer. The Prostate Supplement. 1994; 5:17-22.

Denmeade, et al. A history of prostate cancer treatment. Nat Rev Cancer. 2002; 2(5):389-96.

European office action dated Nov. 6, 2012 for EP Application No. 10704283.0.

Evans, et al. methods for drug discovery: development of potent, selective, orally effective cholecystokinin antagonists. J Med Chem 1988; 31(12):2235-46.

Frey, et al. Pharmacokinetics of 3 prednisolone prodrugs. Evidence of therapeutic inequivalence in renal transplant patients with rejection. Transplantation. Mar. 1985;39(3):270-4.

Gomez-Orellana, I. Strategies to improve oral drug bioavailability. Expert Opin Drug Deliv. May 2005;2(3):419-33.

Griengl, et al. Phosphonoformate and phosphonoacetate derivatives of 5-substituted 2'-deoxyuridines: synthesis and antiviral activity. J Med Chem. Sep. 1988;31(9):1831-9.

Grigoryev, et al. Cytochrome P450c17-expressing *Escherichia coli* as a first-step screening system for 17alpha-hydroxylase-C17,20-lyase inhibitors. Anal Biochem. Feb. 15, 1999;267(2):319-30.

Grigoryev, et al. Effects of new 17alpha-hydroxylase/C(17,20)-lyase inhibitors on LNCaP prostate cancer cell growth in vitro and in vivo. Br J Cancer. Oct. 1999;81(4):622-30.

Haidar, et al. Effects of novel 17alpha-hydroxylase/C17, 20-lyase (P450 17, CYP 17) inhibitors on androgen biosynthesis in vitro and in vivo. J Steroid Biochem Mol Biol. Apr. 2003;84(5):555-62.

Haidar, et al. Novel steroidal pyrimidyl inhibitors of P450 17 (17 alpha-hydroxylase/C17-20-lyase). Arch Pharm (Weinheim). Dec. 2001;334(12):373-4.

Hall. Cytochrome P-450 C21scc: one enzyme with two actions: hydroxylase and lyase. J Steroid Biochem Mol Biol. 1991;40(4-6):527-32.

Handratta, et al. Novel C-17-heteroaryl steroidal CYP17 inhibitors/antiandrogens: synthesis, in vitro biological activity, pharmacokinetics, and antitumor activity in the LAPC4 human prostate cancer xenograft model. J Med Chem. Apr. 21, 2005;48(8):2972-84.

Handratta, et al. Potent CYP17 inhibitors: improved syntheses, pharmacokinetics and anti-tumor activity in the LNCaP human prostate cancer model. J Steroid Biochem Mol Biol. Oct. 2004;92(3):155-65.

Hartmann, et al. Synthesis and evaluation of novel steroidal oxime inhibitors of P450 17 (17 alpha-hydroxylase/C17-20-lyase) and 5 alpha-reductase types 1 and 2. J Med Chem. Nov. 2, 2000;43(22):4266-77.

Huggins, et al. Studies in prostate cancer: The effects of castration on advanced carcinoma of the prostate gland. Arch Surg. 1941; 43(2):209-223.

Humber, et al. Synthesis and biological activity of some cardiotonic compounds related to digitoxigenin. Steroids. Aug. 1983;42(2):189-202.

International search report and written opinion dated Jun. 17, 2009 for PCT/US2010/023391.

International search report dated Oct. 7, 2009 for PCT/US2009/036891.

Jarman, et al. The 16,17-double bond is needed for irreversible inhibition of human cytochrome p45017alpha by abiraterone (17-(3-pyridyl)androsta-5, 16-dien-3beta-ol) and related steroidal inhibitors. J Med Chem. Dec. 31, 1998;41(27):5375-81.

Jefcoate. Measurement of substrate and inhibitor binding to microsomal cytochrome P-450 by optical-difference spectroscopy. Methods Enzymol. 1978;52:258-79.

Jemal, et al. Cancer statistics, 2004. CA cancer J. Clin. 2004; 54(1):8-29.

Kadar, et al. Technical and safety aspects of blood and marrow transplantation using G-CSF mobilized family donors. Transfus Sci. Dec. 1996;17(4):611-8.

Kim, et al. Synergism of cytoplasmic kinases in IL6-induced ligand-independent activation of androgen receptor in prostate cancer cells. Oncogene. Mar. 11, 2004;23(10):1838-44.

Klein, et al. Progression of metastatic human prostate cancer to androgen independence in immunodeficient SCID mice. Nat Med. Apr. 1997;3(4):402-8.

(56) References Cited

OTHER PUBLICATIONS

Laneri, et al. Ionized prodrugs of dehydroepiandrosterone for transdermal iontophoretic delivery. Pharm Res. Dec. 1999;16(12):1818-24.
Ling, et al. 17-Imidazolyl, pyrazolyl, and isoxazolyl androstene derivatives. Novel steroidal inhibitors of human cytochrome C17,20-lyase (P450(17 alpha). J Med Chem. Sep. 26, 1997;40(20):3297-304.
Long, et al. Antiandrogenic effects of novel androgen synthesis inhibitors on hormone-dependent prostate cancer. Cancer Res. Dec. 1, 2000;60(23):6630-40.
Matsunaga, et al. C17,20-lyase inhibitors I. Structure-based de novo design and SAR study of C17,20-lyase inhibitors. Bioorg Med Chem. May 1, 2004;12(9):2251-73.
Matsunaga, et al. Synthetic studies on (1S)-1-(6,7-dimethoxy-2-naphthyl)-1-(1H-imidazol-4-yl)-2-methylpropan-1-ol as a selective C17,20-lyase inhibitor. Tetrahedron: Asymmetry. 2004; 15:2021-2028.
Matsunaga, et al. C(17,20)-lyase inhibitors. Part 2: design, synthesis and structure-activity relationships of (2-naphthylmethyl)-1H-imidazoles as novel C(17,20)-lyase inhibitors. Bioorg Med Chem. Aug. 15, 2004;12(16):4313-36.
McConnell. Physiologic basis of endocrine therapy for prostatic cancer. Urol Clin North Am. Feb. 1991;18(1):1-13.
Mohler, et al. The androgen axis in recurrent prostate cancer. Clin Cancer Res. Jan. 15, 2004;10(2):440-8.
Muscato, et al. Optimal dosing of ketoconazole (KETO) and hydrocortisone (HC) leads to long responses in hormone refractory prostate cancer. Proc ASCO. 1994; 229:701.
Nicolaou, et al. Natural Product-like Combinatorial Libraries Based on Privileged Structures. 1. General Principles and Solid-Phase Synthesis of Benzopyrans. J. Am. Chem. Soc. 2000; 122(41):9939-9953.
NIH Grant Project Reference No. 2RO1 CA27440-24A1, 2R01 CA27440-25A1 Revised Grant Renewal Application, approximate submission date Feb. 18, 2004; approximate award date Sep. 23, 2004.
NIH Grant Project Reference No. 3R)1 CA27440-22S1 Grant Application for Supplemental Funding, approximate date Jun. 21, 2001; approximate award date Aug. 17, 2001.
NIH Grant Project Reference No. 3RO1 CA27440-22S1 Grant Application for Supplemental Funding, approximate date Jun. 21, 2001; approximate award date Aug. 17, 2001.
NIH Grant Project Reference No. 3RO1 CA27440-23S1 Grant Continuation Application and Progress Report, approximate date May 3, 2002; approximate award date Jun. 21, 2002.
NIH Grant Project Reference No. 5R)1 CA27440-24S1 Grant Continuation Application and Progress Report, approximate date Apr. 1, 2003; approximate award date Jun. 3, 2003.
NIH Grant Project Reference No. 5RO1 CA27440-23 Grant Continuation Application and Progress Report, approximate date Jan. 21, 2002; approximate award date Apr. 29, 2002.
NIH Grant Project Reference No. 5RO1 CA27440-24 Grant Continuation Application and Progress Report, approximate date Feb. 20, 2003; approximate award date Jun. 3, 2003.
NIH Grant Project Reference No. 5RO1 CA27440-24S1 Grant Continuation Application and Progress Report, approximate date Apr. 1, 2003; approximate award date Jun. 3, 2003.
NIH Grant Project Reference No. 5RO1 CA27440-25 Grant Renewal Application, approximate submission date Jun. 26, 2003—Unfunded.
NIH Grant Project Reference No. 5RO1 CA27440-26 Grant Continuation Application and Progress Report, approximate submission date Jul. 1, 2005; approximate award date Aug. 2, 2005.
NIH Grant Project Reference No. 5RO1 CA27440-27 Grant Continuation Application and Progress Report, approximate submission date Apr. 26, 2006.
NIH Grant Project Reference No. 5RO1CA27440-27 ESNAP Report, approximate submission date May 8, 2006.
Njar, et al. Inhibitors of 17alpha-hydroxylase/17,20-lyase (CYP17): potential agents for the treatment of prostate cancer. Curr Pharm Des. Mar. 1999;5(3):163-80.
Njar, et al. Novel 17-azoly1 steroids, potent inhibitors of human cytochrome 17 alpha-hydroxylase-C17,20-lyase (P450(17) alpha): potential agents for the treatment of prostate cancer. J Med Chem. Mar. 12, 1998;41(6):902-12.
Njar, et al. Nucleophilic vinylic 'Addition-Elimination' Substitution Reaction of 3B-Acetoxy-17-Chloro-16-Formylandrosta-5,16-Diene: A Novel and General Route to 17-Substituted Steroids Bioorganic and Medical Chemistry Letters 1996; 6(22):2777-27820.
Nnane, et al. Effects of novel 17-azolyl compounds on androgen synthesis in vitro and in vivo. J Steroid Biochem Mol Biol. Dec. 15, 1999;71(3-4):145-52.
O'Donnell, et al. Hormonal impact of the 17alpha-hydroxylase/C(17,20)-lyase inhibitor abiraterone acetate (CB7630) in patients with prostate cancer. Br J Cancer. Jun. 14, 2004;90(12):2317-25.
Office Action dated Jan. 31, 2011 for U.S. Appl. No. 12/577,094.
Office Action dated Mar. 12, 2010 for U.S. Appl. No. 11/817,550.
Office Action dated Apr. 4, 2012 for U.S. Appl. No. 12/577,090.
Office Action dated May 5, 2010 for U.S. Appl. No. 12/577,091.
Office Action dated May 7, 2010 for U.S. Appl. No. 12/577,092.
Office action dated May 12, 2014 for U.S. Appl. No. 13/146,004.
Office Action dated May 23, 2011 for U.S. Appl. No. 12/577,094.
Office Action dated May 25, 2010 for U.S. Appl. No. 12/577,096.
Office Action dated Jun. 1, 2010 for U.S. Appl. No. 12/577,090.
Office Action dated Jun. 1, 2011 for U.S. Appl. No. 12/623,257.
Office Action dated Jun. 2, 2010 for U.S. Appl. No. 11/817,550.
Office Action dated Sep. 8, 2011 for U.S. Appl. No. 12/577,096.
Office Action dated Sep. 9, 2011 for U.S. Appl. No. 12/577,090.
Office action dated Sep. 19, 2013 for U.S. Appl. No. 13/146,004.
Office Action dated Oct. 5, 2011 for U.S. Appl. No. 12/577,094.
Office Action dated Oct. 17, 2012 for U.S. Appl. No. 12/577,090.
Office Action dated Oct. 20, 2010 for U.S. Appl. No. 12/623,257.
Office Action dated Oct. 28, 2010 for U.S. Appl. No. 12/577,091.
Office Action dated Oct. 28, 2010 for U.S. Appl. No. 12/577,092.
Office Action dated Oct. 29, 2010 for U.S. Appl. No. 12/577,090.
Office Action dated Nov. 1, 2010 for U.S. Appl. No. 12/577,096.
Ojida, et al. Stereocontrolled synthesis of (1S)-1-(1H-imidazol-4-yl)-1-(6-methoxy-2-naphthyl)-2-methylpropan-1-ol as a potent C17,20-lyase inhibitor. Tetrahedron: Asymmetry. 2004; 15L1555-1559.
Picard, et al. Synthesis and evaluation of 2'-substituted 4-(4'-carboxy- or 4'-carboxymethylbenzylidene)-N-acylpiperidines: highly potent and in vivo active steroid 5alpha-reductase type 2 inhibitors. J Med Chem. Aug. 1, 2002;45(16):3406-17.
Potter, et al. A convenient, large-scale synthesis of abiraterone acetate [3B-acetoxy-17-(3-pryidyl)androsta-5,16-diene], a potential new drug for the treatment of prostate cancer. Organic Preparations and Procedures Int. 1997; 29(1):123-134.
Potter, et al. Novel steroidal inhibitors of human cytochrome P45017 alpha (17 alpha-hydroxylase-C17,20-lyase): potential agents for the treatment of prostatic cancer. J Med Chem. Jun. 23, 1995;38(13):2463-71.
Randimbivololona, et al. Metabolism and excretion in bile of SC4453, a new semi-synthetic derivative of digoxin following an i.v. bolus injection in the guinea-pig. J Pharmacol. Jan.-Mar. 1984;15(1):53-64.
Recanatini, et al. A new class of nonsteroidal aromatase inhibitors: design and synthesis of chromone and xanthone derivatives and inhibition of the P450 enzymes aromatase and 17 alpha-hydroxylase/C17,20-lyase. Med Chem. Mar. 1, 2001;44(5):672-80.
Ru, et al. Synthesis and Pharmacological Activity of some 17-[2'substituted)-4'-pyrimidyl] androstene derivativies as inhibitors of human 17alpha-hydroxylase/C17,20-lyse., J. Chin. Pharm. Sci., Jun. 2001, vol. 10, No. 1, pp. 3-8.
Small, et al. Ketoconazole retains activity in advanced prostate cancer patients with progression despite flutamide withdrawal. J Urol. Apr. 1997;157(4):1204-7.
Souillac, et al. Characterization of Delivery Systems, Differential Scanning Calorimetry in Encyclopedia of Controlled Drug Delivery, 1999, John Wiley & Sons, pp. 212-227.
Supplementary European Search Report dated Jul. 29, 2009 for European Application No. EP 06736460.

(56) References Cited

OTHER PUBLICATIONS

Thompson, et al. Androgen antagonist activity by the antioxidant moiety of vitamin E, 2,2,5,7,8-pentamethyl-6-chromanol in human prostate carcinoma cells. Mol Cancer Ther. Aug. 2003;2(8):797-803.
Tindall, et al. Symposium on androgen action in prostate cancer. Cancer Res. Oct. 1, 2004;64(19):7178-80.
Trachtenberg, et al. Ketoconazole: a novel and rapid treatment for advanced prostatic cancer. J Urol. Jul. 1983;130(1):152-3.
Vasaitis, et al. Androgen Receptor Inactivation Contributes to Antitumor Efficacy of CYP17 Inhibitor VN/124-1 in Prostate Cancer. Mol. Cancer Therapeutics. 2008; 7(8):2348-2357.
Vasaitis, et al. The Effects of Novel Anti-Androgens on Androgen Receptor Action and Expression. Proceedings of the American Association for Cancer Research. 2006; 47:Abstract 5340. http://aacrmeetingabstracts.org/cgi/content/abstract/2006/1/252-d.
Vippagunta, et al. Crystalline solids. Adv Drug Deliv Rev. May 16, 2001;48(1):3-26.
Zhang, et al. A small composite probasin promoter confers high levels of prostate-specific gene expression through regulation by androgens and glucocorticoids in vitro and in vivo. Endocrinology. Dec. 2000;141(12):4698-710.
Angelastro, M.R. et al., 17 beta-(cyclopropylamino)-androst-5-en-3 beta-ol, a selective mechanism-based inhibitor of cytochrome P450(17 alpha) (steroid 17 alpha-hydroxylase/C17-20 lyase), Biochemical and Biophysical Research Communications, 162(3):1571-1577 (1989).
Armstrong, A.J. et al., A pharmacodynamic study of rapamycin in men with intermediate to high risk localized prostate cancer: A Department of Defense Prosate Cancer Clinical Trials Consortium Trial, Clin. Cancer Res., 16(11):3057-66 (2010).
Auchus, R.J. et al., Use of Prednisone with Abiraterone Acetate in Metastatic Castration-Resistant Prostate Cancer, The Oncologist, 19: 1-10 (2014).
Author Not Known, Definition of Poloxamer, Wikipedia.org, 3 pages, retrieved in May 1, 2014 <http://en.wikipedia.org/wiki/Poloxamer>.
Author Not Known, Highlights of Prescribing Information for Lupron Depot, AbbVie Inc., Chicago, IL, Takeda Pharmaceutical Company, Japan, 26 pages, initial U.S. Approval: 1989, most recent update: 2014.
Author Not Known, Phase I Study of Palomid 529 a Dual TORC1/2 Inhibitor of the PI3K/Art/mTOR Pathway for Advanced Neovascular Age-Related Macular Degeneration (P52901), ClinicalTrials.gov: A Service of the U.S. National Institutes of Health (2012), 3 pages, retrieved on Sep. 16, 2015 <https://clinicaltrials.gov/ct2/show/NCT01033721>.
Ayub, M. et al., Inhibition of testicular 17 alpha-hydroxylase and 17,20-lyase but not 3 beta-hydroxysteroid dehydrogenase-isomerase or 17 beta-hydroxysteroid oxidoreductase by ketoconazole and other imidazole drugs, Journal of Steroid Biochemistry, 28(5):521-531 (1987).
Baldo, P. et al., mTOR pathway and mTOR inihibitors as agents for cancer therapy, Curr. Cancer Drug Targets, 8(8):647-65 (2008). [Abstract Only].
Banks, P.K. et al., Regulation of ovarian steroid biosynthesis by estrogen during proestrus in the rat, Endocrinology, 129(3):1295-1304 (1991).
Barrie, S.E. et al., Inhibition of 17 alpha-hydroxylase/C17-C20 lyase by bifluranol and its analogues, Journal of Steroid Biochemistry, 33(6):1191-1195 (1989).
Berge, et al. Pharmaceutical Salts. Journal of Pharmaceutical Sciences, 66 (1); 1977: 1-17.
Brodie, A.M.H. et al., Inactivation of aromatase in vitro by 4-hydroxy-4-androstene-3,17-dione and 4-acetoxy-4-androstene-3,17-dione and sustained effects in vivo, Steroids, 38(6):693-702 (1981).
Brodie, A.M.H. et al., Studies on the mechanism of estrogen biosynthesis in the rat ovary—I, Journal of Steroid Biochemistry, 7(10):787-793 (1976).
Brodie, A.M.H. Steroidogenesis Pathway Enzymes—Section 9A Introduction, Design of Enzyme Inhibitors as Drugs vol. 2, M. Sandler and H.J. Smith, Oxford University Press, (Ch. 9):414-423 (1993).
Brodie, A.M.H., et al. Lack of evidence for aromatase in human prostatic tissues: effects of 4-hydroxyandrostenedione and other inhibitors on androgen metabolism, Cancer Research, 49(23):6551-6555 (1989).
Brodie, A.M.H., Inhibitors of Steroid Biosynthesis, Design of Enzyme Inhibitors as Drugs vol. 2, M. Sandler and H.J. Smith, Oxford University Press, (Ch.16):503-522 (1993).
Brodie, A.M.H., Steroidogenesis Pathway Enzymes—Aromatase Inhibitors, Design of Enzyme Inhibitors as Drugs vol. 2, M. Sandler and H.J. Smith, Oxford University Press, (Section 9B):424-438 (1993).
Bruno, R. D. et al., 17.alpha.-Hydroxylase/17,20 Lyase Inhibitor VN/124-1 Inhibits Growth of Androgen-independent Prostate Cancer Cells via Induction of theEndoplasmic Reticulum Stress Response, Molecular Cancer Therapeutics, 7 (9), 2828-2836 (2008).
Bruno, R.D. et al., Synthesis and biological evaluations of putative metabolically stable analogs of VN/124-1 (TOK-001): head to head anti-tumor efficacy evaluation of VN/124-1 (TOK-001) and abiraterone in LAPC-4 human prostate cancer xenograft model, Steroids, 76(12):1268-79 (2011).
Bruno, R.D. et al., Targeting cytochrome P450 enzymes: a new approach in anti-cancer drug development, Bioorganic & Medicinal Chemistry, 15(15):5047-5060 (2007).
Bulun, S.E. et al., Use of tissue-specific promoters in the regulation of aromatase cytochrome P450 gene expression in human testicular and ovarian sex cord tumors, as well as in normal fetal and adult gonads, The Journal of Clinical Endocrinology & Metabolism, 77(6):1616-1621 (1993).
Burkhart, J.P. et al., Inhibition of steroid C17(20) lyase with C-17-heteroaryl steroids. Bioorg Med Chem. 4(9):1411-1420 (1996).
Bühler, Pharmaceutical Technology of BASF Excipient, 3rd revised edition, pp. 6-164 (2008).
Chang, S.S., Treatment options for hormone refractory prostate cancer, Rev. Urol., 9 (Suppl 2): S13-S18 (2007).
Chao, J. et al., A versatile synthesis of 17-heterosrylandrostenes via palladium-mediated Suzuki cross-coupling with heteroarylboronic acids, Steroids, 71(7):585-590 (2006).
Chaumeil, J. C., Micronization: A Method of Improving the Bioavailability of Poorly Soluble Drugs, Meth Find Exp Clin Pharmacol 20(3):211-215 (1998).
Chomczynski, P. and Sacchi, N., Single-step method of RNA isolation by acid guanidinium thiocyanate-phenol-chloroform extraction, Analytical Biochemistry, 162(1):156-159 (1987).
Christensen, S.B. et al., Thapsigargin analogues for targeting programmed death of androgen-independent prostate cancer cells, Bioorganic & Medicinal Chemistry, 7(7):1273-1280 (1999).
Church, G.M. and Gilbert, W., Genomic sequencing, Proceedings of the National Academy of Sciences of the USA, 81(7):1991-1995 (1984).
Coen, P. et al., An aromatase-producing sex-cord tumor resulting in prepubertal gynecomastia. The New England Journal of Medicine, 324(5):317-322 (1991).
Cohen, S.M. et al., Comparison of the effects of new specific azasteroid inhibitors of steroid 5 alpha-reductase on canine hyperplastic prostate: suppression of prostatic DHT correlated with prostate regression, The Prostate, 26(2):55-71 (1995).
Communication pursuant to Article 94(3) EPC for EP 10150763.0, 12 pages (Mar. 23, 2012).
Coombes, R.C. et al., 4-Hydroxyandrostenedione treatment for postmenopausal patients with advanced breast cancer, Steroids, 50(1-3):245-252 (1987).
Corbishley, T.P. et al., Androgen Receptor in Human Normal and Malignant Pancreatic Tissue and Cell Lines, Cancer, 57:1992-1995 (1986).
Covey, D.F. et al., 10 beta-propynyl-substituted steroids. Mechanism-based enzyme-activated irreversible inhibitors of estrogen biosynthesis, The Journal of Biological Chemistry, 256(3):1076-1079 (1981).

(56) References Cited

OTHER PUBLICATIONS

De Souza, et al. Enhancement of paclitaxel activity against hormone-refractory prostate cancer cells in vitro and in vivo by quinacrine. Br J Cancer. 1997; 75 (11): 1593-600.
Dehm, S.M., et al., Splicing of a Novel Androgen Receptor Exon Generates a Constitutively Active Androgen Receptor that Mediates Prostate Cancer Therapy Resistance, Cancer Res., 68(13):5469-5477 (2008).
Denmeade, S.R. and Isaacs, J.T., The SERCA pump as a therapeutic target: making a "smart bomb" for prostate cancer, Cancer Biology & Therapy, 4(1):14-22 (2005).
Di Salle, E. et al., Effects of 5 alpha-reductase inhibitors on intraprostatic androgens in the rat, The Journal of Steroid Biochemistry and Molecular Biology, 53(1-6):381-385 (1995).
Dihrendra, K. et al, Solid dispersions: a review, Pak. J. Pharm. Sci., 22(2):234-246 (2009).
Doorenbos, N.J. and Milewich, L., 17-beta-isoxazolyl and 17-beta-pyrazolyl steroids from 3-beta-hydroxy-21-formylpregn-5-en-20-one. Structural assignments, The Journal of Organic Chemistry, 31(10):3193-3199 (1966).
Dorwald, F.Z., Side Reactions in Organic Synthesis: A Guide to Successful Synthesis Design, Weinheim: Wiley-VCH Verlag GmbH and Co. KGaA, Preface, 4 pages (2005).
Duc, I. et al., In vitro and in vivo models for the evaluation of potent inhibitors of male rat 17alpha-hydroxylase/C17,20-lyase, J. Steroid. Biochem. Mol. Biol., 84(5):537-42 (2003).
Eisenhauer, et al. New response evaluation criteria in solid tumours: revises RECIST guideline (version 1.1), Eur. J. Cancer, 45(2): 228-47 (2009).
Elliott, G.B et al. Latent carcinoma of the prostate in a 24-year-old man receiving cyclophosphamide and azathioprine, Can. Med. Assoc. J., 116 (6):651-2 (1977).
Examination Report for GB 1114154.6, 2 pages (May 30, 2013).
Extended European Search Report for EP 10150763.0, 14 pages (Dec. 2, 2010).
Extended European Search Report for EP 10807167.1, 10 pages (Nov. 6, 2012).
Extended European Search Report for EP 10830591.3, 8 pages (Feb. 20, 2013).
Extended European Search Report for EP 12814940.8, 5 pages (May 18, 2015).
Extended European Search Report for EP 12859516.2, 8 pages (May 26, 2015).
Fedorak, et al. A novel colon-specific steroid prodrug enhances sodium chloride absorption in rat colitis. Am J Physiol. Aug. 1995; 269 (2 Pt 1): G210-8.
Feldman, B.J. et al., The development of androgen-independent prostate cancer, Nature Reviews Cancer, 1(1):34-45 (2001).
Ferraldeschi et al, Agents that Target Androgen Synthesis in Castration-Resistant Prostate Cancer., The Cancer J. 19(1) (2013).
Forti, G. et al., Three-month treatment with a long-acting gonadotropin-releasing hormone agonist of patients with benign prostatic hyperplasia: effects on tissue androgen concentration, 5 alpha-reductase activity and androgen receptor content, The Journal of Clinical Endocrinology & Metabolism, 68(2):461-468 (1989).
Frye, S.V. et al., 6-Azasteroids: potent dual inhibitors of human type 1 and 2 steroid 5 alpha-reductase, The Journal of Medicinal Chemistry, 36(26):4313-4315 (1993).
Frye, S.V. et al., 6-Azasteroids: structure-activity relationships for inhibition of type 1 and 2 human 5 alpha-reductase and human adrenal 3 beta-hydroxy-delta 5-steroid dehydrogenase/3-keto-delta 5-steroid isomerase, The Journal of Medicinal Chemistry, 37(15):2352-2360 (1994).
Frye, S.V. et al., Structure-activity relationships for inhibition of type 1 and 2 human 5 alpha-reductase and human adrenal 3 beta-hydroxy-delta 5-steroid dehydrogenase/3-keto-delta 5-steroid isomerase by 6-azaandrost-4-en-3-ones: optimization of the C17 substituent, The Journal of Medicinal Chemistry, 38(14):2621-2627 (1995).
Funke, R. et al., A Phase Ib/II Study Testing the Safety and Efficacy of Combined Inhibition of the PI3K/Akt and Androgen Receptor Signalling Pathways in Castration-resistant Prostate Cancer: GDC-0068 or GDC-0980 with Abiraterone Acetate Versus Abiraterone Acetate, Array Biopharma, TPS2616, 1 page (2012), retrieved on Sep. 25, 2012 <http://www.arraybiopharma.com/_documents/Publication/PubAttachment524.pdf>.
Gaddipati, J.P. et al., Frequent detection of codon 877 mutation in the androgen receptor gene in advanced prostate cancers, Cancer Research, 54(11):2861-2864 (1994).
Garde, D., Tokai Pharmaceuticals' Reformulated Galeterone Demonstrates Robust PSA Reductions in Advanced Prostate Cancer Patients, FierceBiotech, 2 pages, Jan. 2, 2014. URL: http://www.fiercebiotech.com/node/349034/print (Retrieved from the Internet Jul. 28, 2015).
Garrett, R. H. et al. [Editors]. Chapter 8: Lipids. Biochemistry (Second Edition). Saunders College Publishing. pp. 238-258 (1999).
Geller, J. et al., Comparison of prostatic cancer tissue dihydrotestosterone levels at the time of relapse following orchiectomy or estrogen therapy, The Journal of Urology, 132(4):693-696 (1984).
Gold, R. et al., Detection of DNA fragmentation in apoptosis: application of in situ nick translation to cell culture systems and tissue sections, Journal of Histochemistry & Cytochemistry, 41(7):1023-1030 (1993).
Goldman, A.S. et al., Production of male pseudohermaphroditism in rats by two new inhibitors of steroid 17alpha-hydroxylase and C 17-20 lyase, Journal of Endocrinology, 71(3):289-297 (1976).
Goodin, et al. Effect of docetaxel in patients with hormone-dependent prostate-specific antigen progression after local therapy for prostate cancer. J Clin Oncol. May 20, 2005; 23(15): 3352-7. Epub Feb. 28, 2005.
Gormley, G.J., Role of 5 alpha-reductase inhibitors in the treatment of advanced prostatic carcinoma, Urologic Clinics of North America, 18(1):93-98 (1991).
Goss, P.E. et al., Treatment of advanced postmenopausal breast cancer with an aromatase inhibitor, 4-hydroxyandrostenedione: phase II report, Cancer Research, 46(9):4823-4826 (1986).
Goya, S. et al., Studies on cardiotonic steroid analogs, V. : synthesis of 17β(or α)-isoxazolyl and pyrazolyl-16-methyl-14β(or α)-androst-5-enes, Yakugaku Zasshi, 90(5):537-543 (1970) [English Abstract Only].
Gravina, G.L. et al., The TORC1/TORC2 inhibitor, Palomid 529, reduces tumor growth and sensitizes to docetaxel and cisplatin in aggressive and hormone-refractory prostate cancer cells, Endocr. Relat. Cancer, 18(4):385-400 (2011).
Guarna, A. et al., A concise route to 19-nor-10-azasteroids, a new class of steroid 5α-reductase inhibitors. 3.1 synthesis of (+)-19-nor-10-azatestosterone and (+)-17β-(acetyloxy)-(5β)-10-azaestr-1-en-3-one, The Journal of Organic Chemistry, 63(12):4111-4115 (1998).
Guo, Z. et al., A Novel Androgen Receptor Splice Variant is Up-regulated during Prostate Cancer Progression and Promotes Androgen Depletion-Resistant Growth, Cancer Res., 69(6):2305-2313 (2009).
Haase-Held, M. et al., The synthesis of 4-cyanoprogesterone: a potent inhibitor of the enzyme 5-α-reductase, Journal of the Chemical Society, Perkin Transactions 1, 22:2999-3000 (1992).
Habernicht, U.F. et al., Induction of estrogen-related hyperplastic changes in the prostate of the cynomolgus monkey (Macaca fascicularis) by androstenedione and its antagonization by the aromatase inhibitor 1-methyl-androsta-1,4-diene-3,17-dione, The Prostate, 11(4):313-326 (1987).
Haffner, C., Synthesis of 6-azacholesten-3-ones: potent inhibitors of 5alpha-reductase, Tetrahedron Letters, 36(23):4039-4042 (1995).
Hakki, T. and Bernhardt, R., CYP17- and CYPIIB-dependent steroidhydroxylases as drug development targets, Pharmacology & Therapeutics, 111(1):27-52 (2006).
Hamilton, G.A., Chemical models and mechanisms for oxygenases, Molecular Mechanisms of Oxygen Activation, 1:405-451 (1974).
Hamm, R. et al., Patient self-injection: A new approach to administering luteinizing hormone-releasing hormone analogues, 86(7): 840-842 (2000).
Harada, N., Novel properties of human placental aromatase as cytochrome P-450: purification and characterization of a unique form of aromatase, The Journal of Biochemistry, 103(1):106-113 (1988).

(56) References Cited

OTHER PUBLICATIONS

Harlow, et al. Antibodies, a laboratory manual. 1988.
Hartley, T. et al., Endoplasmic reticulum stress response in an INS-1 pancreatic beta-cell line with inducible expression of a folding-deficient proinsulin, BMC Cell Biology, 11:59 (2010).
Henderson, D. et al., Estrogens and benign prostatic hyperplasia: the basis for aromatase inhibitor therapy, 50(1-3):219-233 (1987).
Higuchi and Stella, V., Pro-drugs as novel drug delivery systems. American Chemical Soceity. ACS symposium series 14. (1975).
Hochhaus, et al. A selective HPLC/RIA for dexamethasone and its prodrug dexamethasone-21-sulphobenzoate sodium in biological fluids. Biomed Chromatogr. Nov.-Dec. 1992; 6 (6): 283-6.
Hoehn, W. et al., Human prostatic adenocarcinoma: some characteristics of a serially transplantable line in nude mice (PC 82), The Prostate, 1(1):95-104 (1980).
Holt, D.A. et al., Inhibition of steroid 5 alpha-reductase by unsaturated 3-carboxysteroids, The Journal of Medicinal Chemistry, 33(3):943-950 (1990).
Hsiang, Y.H. et al., The influence of 4-hydroxy-4-androstene-3,17-dione on androgen metabolism and action in cultured human foreskin fibroblasts, Journal of Steroid Biochemistry, 26(1):131-135 (1987).
Hu, R. et al., Ligand-Independent Androgen Receptor Variants Derived from Splicing of Cryptic Exons Signify Hormone-Refractory Prostate Cancer, Cancer Res., 69(1):16-22 (2009).
Hudes, et al. Paciltaxel plus estramustine in metastaic hormone-refractory prostate cancer. Seminars in Oncology, vol. 22, No. 5. Suppl. 12. Oct. 1995, pp. 41-45.
Humez, S. et al., Role of endoplasmic reticulum calcium content in prostate cancer cell growth regulation by IGF and TNFalpha, Journal of Cellular Physiology, 201(2):201-213 (2004).
Hussain, et al., Docetaxel followed by hormone therapy after failure of definitive treatments for clinically localized/locally advanced prostate cancer; preliminary results. Seminars in Oncology, vol. 28, No. 4, Suppl. 15 Aug. 2001, pp. 22-31.
Huynh, C. and Julia, Fixation d'un Group Nitrile en Position 4 des Ceto-3.sub..DELTA..sup.4-Steroides, Bull. Soc. Chim. Fr., 4396, (1971) [English translation of introduction].
Inkster, S. et al., Human testicular aromatase: immunocytochemical and biochemical studies, The Journal of Clinical Endocrinology & Metabolism, 80(6):1941-1947 (1995).
International Search Report and Written Opinion for PCT/US10/044570 (Apr. 29, 2011).
International Search Report and Written Opinion for PCT/US2010/040448 (Feb. 9, 2011).
International Search Report and Written Opinion for PCT/US2010/055996 (Jul. 28, 2011).
International Search Report and Written Opinion for PCT/US2012/071485 (Feb. 27, 2013).
International Search Report for PCT/US2006/007143, 1 page (Aug. 14, 2006).
International Search Report for PCT/US2009/037610, 4 pages (Dec. 1, 2009).
International Search Report for PCT/US2010/023381 (dated Jun. 9, 2010).
International Search Report for PCT/US2010/023387 (Jul. 5, 2010).
International Search Report for PCT/US2012/047253, 5 pages (Dec. 7, 2012).
Ishibashi, K. et al., Synthesis of b-nor-4-aza-5α-androstane compound as 5α-reductase inhibitor, Bioorganic & Medicinal Chemistry Letters, 4(5):729-732 (1994).
Jain, et al. Food and oral antineoplastics: more than meets the eye. Clin Cancer Res. Sep. 1, 2010; 16(17): 4305-7. doi: 10.1158/1078-0432. CCR-10-1857. Epub Aug. 24, 2010.
Jarman, M. et al., Hydroxyperfluoroazobenzenes: novel inhibitors of enzymes of androgen biosynthesis, The Journal of Medicinal Chemistry, 33(9):2452-2455 (1990).
Jarman, M. et al., Inhibitors of enzymes of androgen biosynthesis: cytochrome P450(17) alpha and 5 alpha-steroid reductase. Nat Prod Rep. 15(5):495-512 (1998).

Kitz, R. and Wilson, I.B., Esters of methanesulfonic acid as irreversible inhibitors of acetylcholinesterase, The Journal of Biological Chemistry 237(10):3245-3249 (1962).
Klus, G.T. et al., Growth inhibition of human prostate cells in vitro by novel inhibitors of androgen synthesis, Cancer Research, 56(21):4956-4964 (1996).
Kozák, I. et al., Nuclei of stroma: site of highest estrogen concentration in human benign prostatic hyperplasia, The Prostate, 3(5):433-438 (1982).
Krieg, M. et al., Stroma of human benign prostatic hyperplasia: preferential tissue for androgen metabolism and oestrogen binding, Acta Endocrinologica (Copenhagen), 96(3):422-432 (1981).
Kuppens, I.E.L.M. et al., Oral bioavailability of docetaxel in combination with OC144-093 (ONT-093), Cancer Chemother. Pharmacol., 55: 72-78 (2005).
Kyprianou, N. and Isaacs, J.T., Expression of transforming growth factor-beta in the rat ventral prostate during castration-induced programmed cell death, Molecular Endocrinology, 3(10):1515-1522 (1989).
Kyprianou, N. et al., Programmed cell death during regression of PC-82 human prostate cancer following androgen ablation, Cancer Research, 50(12):3748-3753 (1990).
Labrie, F. et al., Combination therapy for prostate cancer. Endocrine and biologic basis of its choice as new standard first-line therapy, Cancer, 71(3 Suppl):1059-1067 (1993).
Lai, E. et al., Endoplasmic reticulum stress: signaling the unfolded protein response, Physiology (Bethesda, Md.), 22(3):193-201 (2007).
Larsen, J.D. and Bundgaard, H., Prodrug forms for the sulfonamide group. I. Evaluation of N-acyl derivatives, N-sulfonylamidines, N-sulfonylsulfilimines and sulfonylureas as possible prodrug derivatives, Int. J. Pharmaceutics, 37:87-95 (1987).
Larsen, J.D. et al., Prodrug forms for the sulfonamide group. II. Water-soluble amino acid derivatives of N-methylsulfonamides as possible prodrugs, Int. J. Pharmaceutics, 47:103-110 (1988).
Li, J. et al., 4-pregnene-3-one-20β-carboxaldehyde: a potent inhibitor of 17α-hydroxylase/c17,20-lyase and of 5α-reductase, The Journal of Steroid Biochemistry and Molecular Biology, 42(3-4):313-320 (1992).
Li, J. et al., Inhibition of androgen synthesis by 22-hydroximino-23,24-bisnor-4-cholen-3-one, The Prostate, 26(3):140-150 (1995).
Li, J. et al., Synthesis and evaluation of pregnane derivatives as inhibitors of human testicular 17 alpha-hydroxylase/C17,20-lyase, The Journal of Medicinal Chemistry, 39(21):4335-4339 (1996).
Libertini, S.J. et al., Evidence for Calpain-Mediated Androgen Receptor Cleavage as a Mechanism for Androgen Independence, Cancer Res, 67(19):9001-9005 (2007).
Long, B.J. et al., In vitro and in vivo inhibition of LNCaP prostate cancer cell growth by novel inhibitors of androgen synthesis, Proceedings of the American Association for Cancer Research, 90th Annual Meeting, Apr. 10-14, 1999, vol. 40, Abstract #423 (1999).
Lu, Q. et al., Expression of aromatase protein and messenger ribonucleic acid in tumor epithelial cells and evidence of functional significance of locally produced estrogen in human breast cancers, Endocrinology, 137(7):3061-3068 (1996).
Maggiolini, et al. The mutant androgen receptor T877A mediates the proliferative but not the cytotoxic dose-dependent effects of genistein and quercetin on human LNCaP prostate cancer cells. Molecular Pharmacology, vol. 62, pp. 1027-1035, 2002.
Mawhinney, M.G. and Belis, J.A., Androgens and estrogens in prostatic neoplasia, Advances in Sex Hormone Research, 2:141-209 (1976).
McCague, R. et al., Inhibition of enzymes of estrogen and androgen biosynthesis by esters of 4-pyridylacetic acid, The Journal of Medicinal Chemistry, 33(11):3050-3055 (1990).
McDonald, I.A. et al., Inhibition of steroid 5-alpha-reductase by "inverted" competitive inhibitors, Bioorganic and Medicinal Chemistry Letters, 4(6):847-851 (1994).
McLeod, et al., A glucocorticoid prodrug facilitates normal mucosal function in rat colitis without adrenal suppression. Gastroenterology. Feb. 1994; 106 (2): 405-13.

(56) References Cited

OTHER PUBLICATIONS

Metcalf, B.W. et al., Substrate-induced inactivation of aromatase by allenic and acetylenic steroids, Journal of the American Chemical Society, 103(11):3221-3222 (1981).
Montgomery, R.B. et al., Galeterone in men with CRPC: results in four distinct patient populations from the ARMOR2 study, Abstract ∩5029, Poster, Presented at the 50th Annual Meeting of the American Society of Clinical Oncology (ASCO), Chicago, Illinois (May 30, 2014-Jun. 3, 2014).
Moreira, V. et al. Synthesis and evaluation of novel 17-indazole androstene derivatives designed as CYP17 inhibitors, Steroids 72(14):939-948 (2007).
Moreira, V.M. et al., CYP17 inhibitors for prostate cancer treatment—an update, Curr. Med. Chem., 15(9):868-99 (2008).
Nakajin, S. and Hall, P.F., Microsomal cytochrome P-450 from neonatal pig testis. Purification and properties of A C21 steroid side-chain cleavage system (17 alpha-hydroxylase-C17,20 lyase), The Journal of Biological Chemistry, 256(8):3871-3876 (1981).
Nakajin, S. et al., Inhibitory effects and spectral changes in pig testicular cytochrome P-450(17 alpha-hydroxylase/lyase) by 20 beta-hydroxy-C21-steroids, Yakugaku Zasshi (Journal of the Pharmaceutical Society of Japan), 108(12):1188-1195 (1988) [English Abstract Only].
Nakajin, S. et al., Microsomal cytochrome P-450 from neonatal pig testis: two enzymatic activities (17 alpha-hydroxylase and c17,20-lyase associated with one protein, Biochemistry, 20(14):4037-4042 (1981).
Nawrocki, S.T. et al., Bortezomib sensitizes pancreatic cancer cells to endoplasmic reticulum stress-mediated apoptosis, Cancer Research, 65(24):11658-11666 (2005).
Nichimura, et al. Effects of flutamide as a second-line agent for maximum androgen blockade of hormone refractory prostate cancer. Int J Urol. Mar. 2007; 14 (3): 264-7.
Njar, V.C. et al., Synthesis of novel 21-trifluoropregnane steroids: inhibitors of 17 alpha-hydroxylase/17,20-lyase (17 alpha-lyase), Steroids, 62(6):468-473 (1997).
Njar, V.C.O. et al., Novel 10β-aziridinyl steroids; inhibitors of aromatase, Journal of the Chemical Society, Perkin Transactions 1, 10:1161-1168 (1993).
Nnane, I.P. et al., Effects of some novel inhibitors of C17,20-lyase and 5alpha-reductase in vitro and in vivo and their potential role in the treatment of prostate cancer, Cancer Res., 58(17):3826-32 (1998).
Notice of Allowance for U.S. Appl. No. 12/851,070 (May 5, 2014).
Notice of Allowance for U.S. Appl. No. 13/145,997, (May 2, 2014).
Office Action dated Aug. 29, 2013 for U.S. Appl. No. 13/145,997.
Office Action dated Feb. 5, 2015 for U.S. Appl. No. 14/313,894.
Office Action dated Feb. 8, 2013 for U.S. Appl. No. 12/934,135.
Office Action dated Sep. 16, 2013 for U.S. Appl. No. 12/934,135.
Office Action dated Sep. 19, 2013 for U.S. Appl. No. 12/851,070.
Office Action for JP 2007-558143, 7 pages (Mar. 7, 2012).
Office Action for U.S. Appl. No. 12/851,070, 19 pages (Mar. 12, 2013).
Onoda, M. et al., Affinity alkylation of the active site of C21 steroid side-chain cleavage cytochrome P-450 from neonatal porcine testis: a unique cysteine residue alkylated by 17-(bromoacetoxy)progesterone, Biochemistry, 26(2):657-662 (1987).
Pappo, R. and Chorvat, R.J., The synthesis of 2-azasteroids, Tetrahedron Letters, 13(31):3237-3240 (1972).
Partial European Search Report for EP 10150763.0, 6 pages (Jul. 16, 2010).
Pataki, J. and Jensen, E.V., Synthesis of fluorinated 3beta-hydroxypregn-5-en-20-one derivatives, Steroids, 28(4):437-447 (1976).
Pelc, B. and Hodková, J., Androstane derivatives substituted by pyrazole ring in position 17, Collection of Czechoslovak Chemical Communications, 34(2):442-450 (1969).
Petrow, V. and Lack, L., Studies on a 5-alpha-Reductase Inhibitor and Their Therapeutic Implications, The Prostate Cell: Structure and Function, Part B, pp. 283-297 (1981).

Purushottamachar, P. et al., Exploitation of Multi-target Prostate Cancer Clinical Candidate VN/124-1 (TOK-001) to Develop a Novel Class of Androgen Receptor Down Regulating Agents for Prostate Cancer Therapy, Poster, 242nd ACS National Meeting, Aug. 28-Sep. 1, 2011, Paper ID: 11268, 1 page (Aug. 28, 2011).
Purushottamachar, P. et al., Systematic Structure Modifications of Multi-target Prostate Cancer Drug Candidate Galeterone to Produce Novel Androgen Receptor Donw-regulating Agents as an Approach to Treatment of Advanced Prostate Cancer, Journal of Medicinal Chemistry, 79 pages (2013).
Rahmani, M. et al. The kinase inhibitor sorafenib induces cell death through a process involving induction of endoplasmic reticulum stress, Molecular and Cellular Biology, 27(15):5499-5513 (2007).
Rasmusson, G.H. and Toney, J.H., Therapeutic Control of Androgen Action, Annual Reports in Medicinal Chemistry, 29(23):225-232 (1994).
Rasmusson, G.H. et al., Azasteroids as inhibitors of rat prostatic 5 alpha-reductase, The Journal of Medicinal Chemistry, 27(12):1690-1701 (1984).
Rasmusson, G.H. et al., Azasteroids: structure-activity relationships for inhibition of 5 alpha-reductase and of androgen receptor binding, The Journal of Medicinal Chemistry, 29(11):2298-2315 (1986).
Reid, et al., CYP17 inhibition as a hormonal strategy for prostate cancer. Nat Clin Pract Urol. Nov. 2008; 5 (11): 610-20.
Remington: The Science and Practice of Pharmacy, Nineteenth Ed., Mack Publishing Co., Easton, Pennsylvania, (1995).
Rittmaster, R.S. et al., Differential effect of 5 alpha-reductase inhibition and castration on androgen-regulated gene expression in rat prostate, Molecular Endocrinology, 5(7):1023-1029 (1991).
Ron, D. and Walter, P., Signal integration in the endoplasmic reticulum unfolded protein response, Nature Reviews Molecular Cell Biology, 8(7):519-529 (2007).
Russell, D.W. and Wilson, J.D., Steroid 5 alpha-reductase: two genes/ two enzymes, Annual Review of Biochemistry, 63:25-61 (1994).
Saad, et al. The Canadian Uro-Oncology Group multicentre phase II study of docetaxel administered every 3 weeks with prednisone in men with metastatic hormone-refractory prostate cancer progressing after mitoxantrone/prednisone. BJU Int. Aug. 5, 2008; 102 (5); 551-5, doi: 10.1111/j.1464-410X.2008.07733.x Epub May 28.
Saulnier, et al. An efficient method for the synthesis of guanidino prodrugs. Bioorganic and Medicinal Chemistry Letters. 1994; 4(16):1985-1990.
Schayowitz, A. et al., Prolonging hormone sensitivity in prostate cancer xenografts through dual inhibition of AR and mTOR, Br. J. Cancer, 103(7):1001-7 (2010).
Schayowitz, et al. Synergistic effect of a novel antiandrogen, VN/124-1 and signal transduction inhibitors in prostate cancer progression of hormone independence in vitro. Mol. Cancer Ther., vol. 7 (1), pp. 121-132, Jan. 2008.
Schayowitz. Synergistic effect of anti-androgens and signal transduction inhibitors in prostate cancer progression, University of Maryland Baltimore Thesis, 186 pages (2008).
Schieweck, K. et al., Anti-tumor and endocrine effects of non-steroidal aromatase inhibitors on estrogen-dependent rat mammary tumors, The Journal of Steroid Biochemistry and Molecular Biology, 44(4-6):633-636 (1972).
Schwarzel, W.C. et al., Studies on the mechanism of estrogen biosynthesis. 8. The development of inhibitors of the enzyme system in human placenta, Endocrinology, 92(3):866-880 (1993).
Shao, T.C. et al., Effects of finasteride on the rat ventral prostate, Journal of Andrology, 14(2):79-86 (1993).
Shearer, R. and Davies, J.H., Studies in Prostatic Cancer with 4-Hydroxyandrostenedione, 4-hydroxyandrostenedione—A new approach to hormone-dependent cancer, Royal Society of Medicine Services, Limited, Ed. Coombes, R.C. and Dowsett, M., Royal Society of Medicine Services International Congress and Symposium Series No. 180, pp. 41-44 (1991).
Simmons, et al. Combined androgen blockade revisited: emerging options for the treatment of castration-resistant prostate cancer. Urology. Apr. 2009; 73 (4): 697-705.
Sinkula, J.A. and Yalkowsky, S.H., Rationale for design of biologically reversible drug derivatives: prodrugs, J. Pharm. Sci., 64(2):181-210 (1975).

(56) References Cited

OTHER PUBLICATIONS

Sjoerdsma, A., Suicide enzyme inhibitors as potential drugs, Clinical Pharmacology & Therapeutics, 30(1):3-22 (1981).
Skryma, R. et al., Store depletion and store-operated Ca2+ current in human prostate cancer LNCaP cells: involvement in apoptosis, The Journal of Physiology, 527(Pt 1):71-83 (2000).
Snider, C.E. and Brueggemeier, R.W., Covalent modification of aromatase by a radiolabeled irreversible inhibitor, Journal of Steroid Biochemistry, 22(3):325-330 (1985).
Stangelberger, et al. The combination of antagonists of LHRH with antagonists of GHRH improves inhibition of androgen sensitive MDA-PCa-2b and LuCaP-35 prostate cancers. Prostate. Sep. 1, 2007; 67 (12): 1339-53.
STN Registry No. 851983-85-2, CAS Registry, 1 page, entered STN Jun. 9, 2005.
Stoner, E., The clinical development of a 5 alpha-reductase inhibitor, finasteride, The Journal of Steroid Biochemistry and Molecular Biology 37(3):375-378 (1990).
Szendi, Z. et al., Steroids, LIII: new routes of aminosteroids[1], Monatshefte für Chemie Chemical Monthly, 127(11):1189-1196 (1996).
Tepper, C.G. et al., Characterization of a Novel Androgen Receptor Mutation in a Relapsed CWR22 Prostate Cancer Xenograft and Cell Line, Cancer Research, 62:6606-6614 (2002).
Trachtenberg, J., Ketoconazole therapy in advanced prostatic cancer, The Journal of Urology, 132(1):61-63 (1984).
Tunn, U.W. et al., Comparison of LH-RH analogue 1-month depot and 3-month depot by their hormone levels and pharmacokinetic profile in patients with advanced prostate cancer, 60(Suppl. 1): 9-17 (1998).
UK Examination report dated Sep. 27, 2013 for GB Application No. 1114153.8.
UK Examination report dated Oct. 8, 2014 for GB Application No. 1114153.8.
UK Examination report dated Nov. 21, 2014 for GB Application No. 1114153.8.
UK Examination report dated Nov. 21, 2014 for GB Application No. 1416433.9.
Vakatkar, V.V. et al., Cleavage of steriodal oximes, semicarbazones and thiosemicarbazones with titanous chloride under mild conditions, Abstract, Chemistry and Industry, Society of Chemical Industry, London, No. 17, p. 742 (1977).
Van Steenbrugge, G.J. et al., Transplantable human prostatic carcinoma (PC-82) in athymic nude mice. III. Effects of estrogens on the growth of the tumor tissue, The Prostate, 12(2):157-171 (1988).
Vehring. Pharmaceutical particle engineering via spray drying. Pharm Res. May 2008;25(5):999-1022. Epub Nov. 28, 2007.
Veldscholte, J. et al., Anti-androgens and the mutated androgen receptor of LNCaP cells: differential effects on binding affinity, heat-shock protein interaction, and transcription activation, Biochemistry, 31(8):2393-2399 (1992).
Vescio, R.A. et al., Cancer biology for individualized therapy: correlation of growth fraction index in native-state histoculture with tumor grade and stage, Proceedings of the National Academy of Sciences of the USA, 87(2):691-695 (1990).
Visakorpi, T. et al., In vivo amplification of the androgen receptor gene and progression of human prostate cancer, Nature Genetics 9(4):401-406 (1995).
Voets, M. et al., Heteroaryl-substituted naphthalenes and structurally modified derivatives: selective inhibitors of CYP11B2 for the treatment of congestive heart failure and myocardial fibrosis. J Med Chem. 48(21):6632-6642 (2005).
Wainstein M.A. et al., CWR22: androgen-dependent xenograft model derived from a primary human prostatic carcinoma, Cancer Research, 54(23):6049-6052 (1994).
Weintraub, P.M. et al., Chemical Abstract No. 116:214776V for EP 0469547, Chemical Abstracts Service, American Chemical Society, Columbus, OH, 116(22):778 (1992).
Weintraub, P.M. et al., Chemical Abstract No. 117 for EP 0469-548 A2, Steroids, 117:985 (1992).
Wicha, J. and Masnyk, M., Cardiotonic Steroids, Part 8., Synthesis of 17beta-(3'-Pyridyl)-14beta-androst-4-ene-3beta, 14-diol from 17-Oxandrostane Derivatives, Bulletin of the Polish Academy of Sciences, Chemistry, 33(1-2):19-27 (1985).
Wilkinson, G.R., Chapter One: Pharmacokinetics, The Dynamics of Drug Absorption, Distribution, and Elimination, Goodman and Gilman's The Pharmaological Basis of Therapeutics, 10th Supp. Edition, 2 pages (2001).
Williams, G. et al., Objective responses to ketoconazole therapy in patients with relapsed progressive prostatic cancer, British Journal of Urology, 58(1):45-51 (1986).
Written Opinion for PCT/US2006/007143, 4 pages (Aug. 14, 2006).
Written Opinion for PCT/US2009/037610, 5 pages (Dec. 1, 2009).
Written Opinion for PCT/US2012/047253, 9 pages (Dec. 7, 2012).
Wu, J. and Kaufman, R.J., From acute ER stress to physiological roles of the Unfolded Protein Response, Cell Death & Differentiation, 13(3):374-384 (2006).
Yen, W.C. et al., Differential effect of taxol in rat primary and metastatic prostate tumors: site-dependent pharmacodynamics, Pharmaceutical Research, 13(9):1305-1312 (1996).
Yue, W. et al., A new nude mouse model for postmenopausal breast cancer using MCF-7 cells transfected with the human aromatase gene, Cancer Research, 54(19):5092-5095 (1994).
Yue, W., et al. Effect of aromatase inhibitors on growth of mammary tumors in a nude mouse model, Cancer Research, 55(14):3073-3077 (1995).
Zenger, M. et al., Structure-Activity Relationship and Drug Design, Remington's Pharmaceutical Sciences (Sixteenth Edition), Mack Publishing, Chapter 27: 420-425 (1980).
Zheng, J.Y. and Fulu, M., Decrease of genital organ weights and plasma testosterone levels in rats following oral administration of leurpolide microemulsion, International Journal of Pharmaceutics, 307: 209-215 (2006).
Zhou, J.L. and Brodie, A., The effect of aromatase inhibitor 4-hydroxyandrostenedione on steroid receptors in hormone-dependent tissues of the rat, The Journal of Steroid Biochemistry and Molecular Biology, 52(1):71-76 (1995).
Zhuang, Q.Y. et al., [Effects of rapamycin on prostate cancer PC-3 cells], Ai Zheng, 28(8):851-5 (2009) [English Abstract Only].

PRODRUGS OF STEROIDAL CYP17 INHIBITORS/ANTIANDROGENS

CROSS-REFERENCE

This application claims the benefit of U.S. Provisional Application No. 61/150,031, filed Feb. 5, 2009, and which is incorporated herein by reference in its entirety

FIELD OF THE INVENTION

This invention provides novel prodrugs of steroidal CYP17 inhibitors for the treatment of urogenital and/or androgen-related cancers, diseases and/or conditions, including castrate-resistant prostrate cancer, the synthesis of these new chemical entities, and to methods of using the same in the treatment of urogenital and/or androgen-related cancers, diseases and/or conditions.

BACKGROUND OF THE INVENTION

Prostate cancer (PCA) is the most common malignancy and age-related cause of cancer death worldwide. Apart from lung cancer, PCA is the most common form of cancer in men, and the second leading cause of death in American men. In the United States in 2008, an estimated 186,320 new cases of prostate cancer were expected to be diagnosed and about 28,660 men were expected to die of this disease, with African American men and Jamaican men of African decent having the highest incidence rates thereof in the world (American Cancer Society—Cancer Facts and Figures 2008).

Androgens play an important role in the development, growth, and progression of PCA (McConnell, J. D., *Urol. Clin. North Am.*, 1991, 18: 1-13), with the two most important androgens in this regard being testosterone, 90% of which is synthesized in the testes and the remainder (10%) is synthesized by the adrenal glands, and the more potent androgen, dihydrotestosterone (DHT), to which testosterone is converted by the enzyme steroid, 5α-reductase, that is localized primarily in the prostate (Bruchovsky, N. et al., *J. Biol. Chem.*, 1968, 243, 2012-2021).

Huggins et al. introduced androgen deprivation as a therapy for advanced and metastatic PCA in 1941 (Huggins, C. et al., *Arch. Surg.*, 1941, 43, 209-212), and since then, androgen ablation therapy has been shown to produce the most beneficial responses in multiple settings in PCA patients (Denmeade, S. R. et al., *Nature Rev. Cancer*, 2002, 2: 389-396). Orchiectomy (either surgical, or medical with a GnRH agonist) remains the standard treatment option for most prostate cancer patients, reducing or eliminating androgen production by the testes, but not affecting androgen synthesis in the adrenal glands. Several studies have reported that a combination therapy of orchiectomy with antiandrogens to inhibit the action of adrenal androgens significantly prolongs the survival of PCA patients (Crawford, E. D. et al., *New Engl. J. Med.*, 1989, 321, 419-424; Crawford, E. D. et al., *J. Urol.*, 1992, 147: 417A; and Denis, L., *Prostate*, 1994, 5 (Suppl.), 17s-22s).

In a recent featured article by Mohler and colleagues (Mohler, J. L. et al., *Clin. Cancer Res.*, 2004, 10, 440-448) it was clearly demonstrated that testosterone and dihydrotestosterone occur in recurrent PCA tissues at levels sufficient to activate androgen receptors. In addition, using microarray-based profiling of isogenic PCA xenograft models, Sawyer and colleagues (Chen, C. D. et al., *Nat. Med.*, 2004, 10, 33-39) found that a modest increase in androgen receptor mRNA was the only change consistently associated with the development of resistance to antiandrogen therapy. Potent and specific compounds that inhibit androgen synthesis in the testes, adrenals, and other tissue may therefore be a more effective for the treatment of PCA (Njar, V. C. O. and Brodie, A. M. H., *Current Pharm. Design*, 1999, 5: 163-180).

In the testes and adrenal glands, the last step in the biosynthesis of testosterone involves two key reactions that occur sequentially, both reactions being catalyzed by a single enzyme, the cytochrome P450 monooxygenase 17α-hydroxylase/$_{17,20}$-lyase (CYP17) (Hall, P. F., *J. Steroid Biochem. Molec. Biol.*, 1991, 40, 527-532). Ketoconazole, an antifungal agent that also inhibits P450 enzymes, is also a modest CYP17 inhibitor, and has been used clinically for the treatment of PCA (Trachtenberg, J. et al., *J. Urol.* 1983, 130, 152-153). It has been reported that careful scheduling of treatment can produce prolonged responses in otherwise castrate-resistant prostate cancer patients (Muscato, J. J. et al., *Proc. Am. Assoc. Cancer Res.*, 1994, 13: 22 (Abstract)). Further, ketoconazole was found to retain activity in advanced PCA patients with progression, despite flutamide withdrawal (Small, E. J. et al., *J. Urol.*, 1997, 157, 1204-1207), and although the drug has now been withdrawn from use because of liver toxicity and other side effects, the ketoconazole results suggest that more potent and selective inhibitors of CYP17 could provide useful agents for treating this disease, even in advanced stages, and in some patients who may appear to be hormone refractory.

A variety of potent steroidal and non-steroidal inhibitors of CYP17 have been reported, some of which having been shown to be potent inhibitors of testosterone production in rodent models (Njar and Brodie, op. cit.). Recently, Jarman and colleagues have described the hormonal impact of their most potent CYP17 inhibitor, abiraterone, in patients with prostate cancer (O'Donnell, A. et al., *Br. J. Cancer*, 2004, 90: 2317-2325). Some potent CYP17 inhibitors have been shown to also inhibit 5α-reductase and/or be potent antiandrogens with potent antitumor activity in animal models (Njar and Brodie, op. cit., and Long, B. J. et al., *Cancer Res.*, 2000, 60, 6630-6640).

In addition to abiratcronc and to related publications from Barrie and Jarman, Njar et al. disclosed a series of potent CYP17 inhibitors/antiandrogens, the 17-benzazoles, 17-pyrimdinoazoles and 17-diazines in Published International Patent Application WO2006/093993 (University of Maryland). These compounds are potent inhibitors of human CYP17 enzyme, as well as potent antagonists of both wild type and mutant androgen receptors (AR). Particularly-potent CYP17 inhibitors included 3-β-hydroxy-17-(1H-benzimidazole-1-yl)androsta-5,16-diene (Compound 5), 17-(1H-benzimidazole-1-yl)androsta-4,16-diene-3-one (Compound 6), and 3-β-hydroxy-17-(5'-pyrimidyl)androsta-5,16-diene (Compound 15), with $IC_{50}$ values of 300, 915 and 500 nM, respectively.

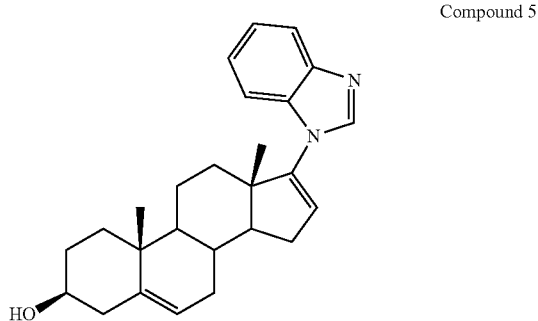

Compound 5

Compound 6

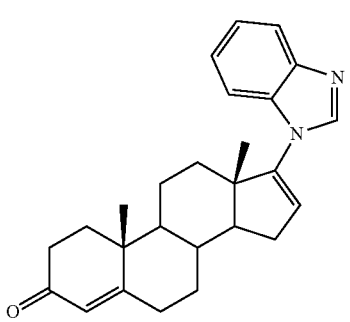

Compound 15

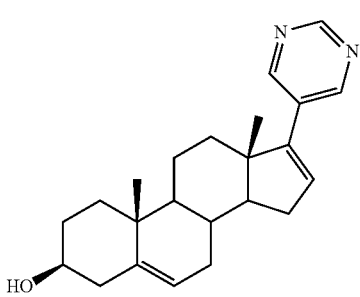

Compounds 5, 6, and 15 were effective at competing with the binding of $^3$H-R1881 (methyltrienolone, a stable synthetic androgen) to both the mutant LNCaP A and the wild-type AR, with a 2.2- to 5-fold higher binding efficiency to the latter. Compounds 5 and 6 were also shown to be potent pure AR antagonists, with cell-growth studies showing that Compounds 5 and 6 inhibit the growth of DHT-stimulated LNCaP and LAPC4 prostate cancer cells with $IC_{50}$ values in the low micromolar range (i.e., <10 µM). Their inhibitory potencies were comparable to that of casodex, but remarkably superior to that of flutamide.

The pharmacokinetics of compounds 5 and 6 in mice showed that following s.c. administration of 50 mg/kg of compounds 5 and 6, peak plasma levels of 16.82 and 5.15 ng/mL, respectively, occurred after 30 to 60 minutes, both compounds were cleared rapidly from plasma (terminal half-lives of 44.17 and 39.93 minutes, respectively), and neither was detectable at 8 hours. Compound 5 was rapidly converted into a metabolite, tentatively identified as 17-(1H-benzimidazol-1-yl)androsta-3-one.

When tested in vivo, compound 5 proved to be very effective at inhibiting the growth of androgen-dependent LAPC4 human prostate tumor xenograft, while compound 6 proved to be ineffective. Administration of compound 5 (50 mg/kg, twice daily) resulted in a 93.8% reduction (P=0.00065) in the mean final tumor volume compared with controls, and it was also significantly more effective than castration. This was the first example of an anti-hormonal agent (an inhibitor of androgen synthesis (CYP17 inhibitor)/antiandrogen) that is significantly more effective than castration in suppression of androgen-dependent prostate tumor growth. In view of these impressive anti-cancer properties, compound 5 and analogs may be used for the treatment of human prostate cancer, as well as breast cancer, ovarian cancer, and other urogenital cancers or other androgen-related conditions or diseases.

In addition to a compound's efficacy, oral bioavailability is also often an important consideration for the development of molecules as therapeutic agents. The calculated physical properties of Compound 5, for example, satisfies both the Lipinski "rule of five" (Lipinski, C. A., *J Pharmacol Toxicol Methods* 2000, 44, (1), 235-49) and the recently-proposed rule by Veber et al. (Veber, D. F. et al., *J Med Chem* 2002, 45, (12), 2615-23) for predicting an improved likelihood of high or drug-like oral bioavailability for new drug candidates, as presented for Compound 5 in Table 1. These data suggest that the compound should be orally bioavailable and, as such, a strong drug candidate.

TABLE 1

Molecular Properties of Compound 5 (VN/124-1) Based on Lipinski's and Verber's Criteria

|  | Limit | VN/124-1 | Results |
|---|---|---|---|
| A. Lipinski Criterion |  |  |  |
| Hydrogen bond donors | ≤5 | 1 | Pass |
| Hydrogen bond acceptors | ≤10 | 2 | Pass |
| Molecular weight | ≤500 | 388.2515 | Pass |
| CLogP | <5 | 5.822 | Fail |
| B. Veber's Criterion |  |  |  |
| Number of rotatable bonds | ≤10 | 1 | Pass |
| Polar surface area | ≤140°$A^2$ | 38.05°$A^2$ | Pass |
| Sum of hydrogen bond donors and acceptors | ≤12 | 3 | Pass |

However, some initial studies have indicated that compound 5 has low (~10%) oral bioavailability in rats. On the basis of the Lipinski's rule, compound 5 has a higher cLogP value (i.e., >5), which could be the major reason for the finding of poor oral bioavailability, as is typical of many steroids. Because oral administrations of drugs are generally preferred, it is important to find ways to improve the oral bioavailability of steroids exemplified by compound 5, as well as the other compounds presented in WO2006/093993.

Additionally, modifications of a compound's structure, such that the serum half-life is extended and $C_{max}$ is delayed, are desired, due to better dosing regimens and consistent delivery of the drug to the target in a single dosing.

Further background of the invention is contained in U.S. Pat. No. 5,604,213 (Barrie et al); U.S. Pat. No. 5,994,335 (Brodie et al); U.S. Pat. No. 6,200,965 (Brodie et al); and, U.S. Pat. No. 6,444,683 (Brodie et al).

Certain references cited herein are incorporated by reference in their entirety.

SUMMARY OF THE INVENTION

In some embodiments, the invention contemplates a compound of Formula I:

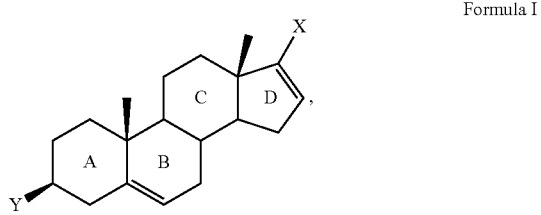

Formula I wherein:
the ABC ring structure is optionally substituted independently at each position and wherein hydrogen substituents on adjacent carbon atoms of the ABC ring structure are optionally removed and replaced by a pi-bond between the adjacent carbon atoms;

Y is Z-L-C(=O)O—; and
either
X is an optionally substituted heterocycle that is a pyridine, pyrazine, pyrimidine, pyridazine, benzimidazole, benzotriazole, pyrimidinoimidazole, or pyrimidinotriazole group, wherein the benzimidazole, benzotriazole, pyrimidinoimidazole or pyrimidinotriazole group is bonded to the C17 position through a nitrogen atom on a 5-membered ring of the heterocycle, and the pyridine, pyrazine, pyrimidine, or pyridazine group is bonded to the C17 position through a carbon atom of the heterocycle;

L is $C_1$-$C_{12}$-alkyl, fluoro-$C_2$-$C_6$-alkyl, aryl, arylalkyl, alkylaryl, alkoxyalkyl, polyalkoxyalkyl, or heteroaryl, any of which is optionally cyclic or together with Z forms a ring, wherein L is optionally substituted with one or more of alkyl, arylalkyl, alkylaryl, alkylheteroaryl, halogen, hydroxyl, alkoxy, and mercaptan; and Z is a charged group that is charged under normal physiological conditions, wherein the charged group is a sulfonic acid; a phosphonic acid; a fluoroalkanol; or an acidic hydroxyl group, or
X is an optionally-substituted pyridine group;

L is $C_1$-$C_{12}$-alkyl, fluoro-$C_2$-$C_6$-alkyl, aryl, arylalkyl, alkylaryl, alkoxyalkyl, polyalkoxyalkyl, or heteroaryl, any of which is optionally cyclic or together with Z forms a ring, wherein L is optionally substituted with one or more of alkyl, arylalkyl, alkylaryl, alkylheteroaryl, halogen, hydroxyl, alkoxy, alkylamino, and mercaptan; and Z is a charged group that is charged under normal physiological conditions, wherein the charged group is a quaternary ammonium group of the formula $(R_3N^+)$—, wherein each R group is independently $C_1$-$C_7$-branched alkyl, $C_1$-$C_7$-straight-chain alkyl, aryl, alkylaryl, aralkyl, heteroaryl, or two or more R groups together form a ring; a sulfonic acid; a phosphonic acid; a fluoroalkanol; or an acidic hydroxyl group, or a pharmaceutically-acceptable salt thereof.

In some embodiments, the invention contemplates a pharmaceutical composition comprising a therapeutically-effective amount of one or more compounds of the invention and one or more pharmaceutically-acceptable excipients, bulking agents, binders, flow agents, release agents, carriers or diluents.

In some embodiments, the invention contemplates a method of treating a cancer or a urogenital disease in a subject in need or want thereof, the method comprising administering to the subject a therapeutically-effective amount of a compound of the invention.

In some embodiments, the invention contemplates a method of treating a cancer or a urogenital disease in a subject in need or want thereof, the method comprising administering to the subject a therapeutically-effective amount of a compound of the invention, in combination with a hormone therapy, a chemotherapy, a radiation therapy, an immunotherapy, or surgery.

DETAILED DESCRIPTION OF THE INVENTION

As used herein, the following terms have the following definitions, unless otherwise specified.

Alkyl is a $C_1$-$C_{12}$-straight, $C_1$-$C_{12}$-branched, or $C_3$-$C_{12}$-cyclic group, optionally substituted independently at each position with one or more of hydroxyl, methoxy, ethoxy, sulfhydryl, methylmercapto, ethylmercapto, fluorine, chlorine, bromine, iodine, aryl, and heteroaryl.

Aryl is a mono- or poly-cyclic aromatic system. Non-limiting examples of aryl include phenyl, naphthyl, indenyl, fluorenyl, phenathrenyl, and azulenyl. Aryl is optionally substituted independently at each position with one or more of hydroxyl, methoxy, ethoxy, sulfhydryl, methylmercapto, ethylmercapto, fluorine, chlorine, bromine, iodine, oxo, and heteroaryl. In some embodiments, aryl groups contain from five to ten ring atoms.

Heteroaryl is a mono- or poly-cyclic aromatic system comprising at least one aromatic ring with at least one ring heteroatom, wherein the heteroatom is nitrogen, oxygen, or sulfur. Heteroaryl is optionally substituted independently at each position with hydroxyl, methoxy, ethoxy, sulfhydryl, methylmercapto, ethylmercapto, fluorine, chlorine, bromine, iodine, oxo and aryl. Non-limiting examples of heteroaryl groups include furan, thiophene, pyrrole, pyrrazole, imidazole, oxazole, isoxazole, thiazole, isothiazole, triazole, thiadiazole, oxadiazole, pyridine, pyrimidine, pyrazine, pyridazine, triazine, indole, carbazole, benzofuran, benzothiphene, benzthiazole, indazole, quinoline, isoquinoline, cinnoline, and phthalazine. In some embodiments, heteroaryl groups contain from five to twelve ring atoms.

Alkylaryl is an alkyl group that is distally attached via an aryl group, for example, tolyl.

Aralkyl is an aryl group that is distally attached via an alkyl group, for example, benzyl.

Polyalkoxyl is polypropylene glycol) or poly(ethylene glycol), wherein the monomers are repeated 2-100 times, wherein such polyalkoxy groups may be defined by the precise range of repeating units (e.g., 35-40), by the targeted peak of envelope distribution in the repeating units (e.g., 114 from PEG5000), or by a selection for solubility or physical properties, and wherein such groups are optionally "capped" by an alkyl group (MPEG5000 for methoxy-PEG5000) or an aryl group, such as phenyl (polyalkoxylaryl).

Numbering of the steroid core as used herein is:

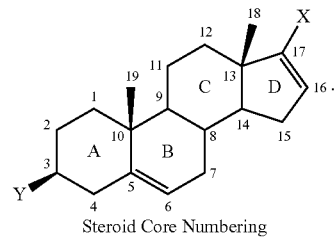

Steroid Core Numbering

The instant invention contemplates the use of prodrugs, (modified versions or precursors of a parent compound, designed to enhance delivery properties and be converted to the parent compound in the body in a predictable, consistent manner) to improve oral bioavailability and pharmacokinetics of effective therapeutic agents. The invention provides prodrugs of steroidal C-17 heterocycles, and methods of synthesizing and using the same to treat urogenital and/or androgen-related cancers, diseases and conditions.

In some embodiments, a prodrug of the invention comprises a prodrug group at the 3-carbon on the "A" ring of the compound. In some embodiments, the prodrug group comprises an ester linkage. In some embodiments, the prodrug group is attached to the A-ring by the ester linkage. In some embodiments, the prodrug group comprises a charged group. A charged group is a group that is charged under normal physiological conditions. Non-limiting examples of a charged group include trialkylammonium groups, quaternary ammonium groups, sulfonic acids, phosphonic acids, fluoroalkanols; or acidic hydroxyl groups. In some embodiments, an acidic hydroxyl group is made acidic by the resonance and/or inductive effect of a nearby electron-withdrawing group. In some embodiments, an acidic hydroxyl group is made acidic by the resonance and/or inductive effect of a nearby electron-withdrawing group, wherein the acidic hydroxyl group is more acidic than an analogous hydroxyl group lacking the nearby electron-withdrawing group. In some embodiments, the acidic hydroxyl group is more acidic than water. In some embodiments, the acidic hydroxyl group is phenolic. In some embodiments, the acidic hydroxyl group has a substantial negative charge in water. In some embodiments, the acidic hydroxyl group exists substantially as an alkoxide in water. In some embodiments, the acidic hydroxyl group has a substantial negative charge in physiological fluids. In some embodiments, the acidic hydroxyl group has a substantial negative charge under normal physiological conditions. In some embodiments, the acidic hydroxyl group exists substantially as an alkoxide under normal physiological conditions. In some embodiments, normal physiological conditions are conditions inherent in a living organism.

In some embodiments, the charged group is connected to the ester linkage by a linking group. In some embodiments, the linking group is $C_1$-$C_{12}$-alkyl, fluoro-$C_2$-$C_6$-alkyl, aryl, arylalkyl, alkylaryl, alkoxyalkyl, polyalkoxyalkyl, or heteroaryl. In some embodiments, the linking group is cyclic. In some embodiments, the linking group together with the charged group forms a ring. In some embodiments, the linking group is optionally substituted with one or more of alkyl, aryl, heteroaryl, aralkyl, alkylaryl, halogen, hydroxyl, alkoxy, alkylamino, and mercaptan.

In some embodiments, the prodrug group is a quaternary ammonium species, for example, betaine, carnitine, and cocamidopropylbetaine (CAPB). In some embodiments, the prodrug group is an oxycarbonylalkylphosphonate; an oxycarbonylalkylsulfonate; or a phenolic carboxylate, such as syringic acid or gallic acid, or a pharmaceutically-acceptable salt of any such compound. The invention also contemplates synthetic analogs of these compounds. In some embodiments, the synthetic analog has improved bioavailability. In some embodiments, the synthetic analog has improved pharmacokinetics. In some embodiments, the prodrug group fragments in vivo to provide a drug.

In some embodiments, a prodrug fragments under a set of physiological conditions. In some embodiments, the set of physiological conditions that fragment a prodrug is general. In some embodiments, the set physiological conditions that fragment a prodrug is specific to the identity of the prodrug. In some embodiments, the set of physiological conditions comprises pH. In some embodiments, the set of physiological conditions comprises temperature. In some embodiments, the set of physiological conditions comprises metabolism. In some embodiments, the set of physiological conditions comprises hydrolysis. In some embodiments, the set of physiological conditions comprises catalysis. In some embodiments, the set of physiological conditions comprises enzyme activity. In some embodiments, the set of physiological conditions comprises oxidation or reduction.

In some embodiments, the optional substitution for the ABC ring structure includes one or more of: $C_1$-$C_6$-alkyl; halogenated $C_1$-$C_6$-alkyl; $C_1$-$C_6$-alkenyl; halogenated $C_1$-$C_6$-alkenyl; halogen; amino; aminoalkylene; hydroxyimino; and hydroxy. In some embodiments, an alkenyl group is bonded to the ABC ring structure by an $sp^3$ carbon of the alkenyl group. In some embodiments, an alkenyl group is bonded to the ABC ring structure by an $sp^2$ carbon of the alkenyl group. In some embodiments, hydrogen substituents on adjacent carbon atoms of the ABC ring structure are removed and replaced by a pi-bond between the adjacent carbon atoms.

In some embodiments, the pyridine, pyrazine, pyrimidine, pyridazine, benzimidazole, benzotriazole, pyrimidinoimidazole, or pyrimidinotriazole functionalities attached to the D ring are optionally substituted with one or more of halogen, amino, aminoalkylene, hydroxy, —SH, —S—$C_1$-$C_6$-alkyl, $C_1$-$C_6$-alkyl and halogenated $C_1$-$C_6$-alkyl.

In some embodiments, the pyridine, pyrazine, pyrimidine, pyridazine, benzimidazole, benzotriazole, pyrimidinoimidazole, and pyrimidinotriazole groups are, respectively:

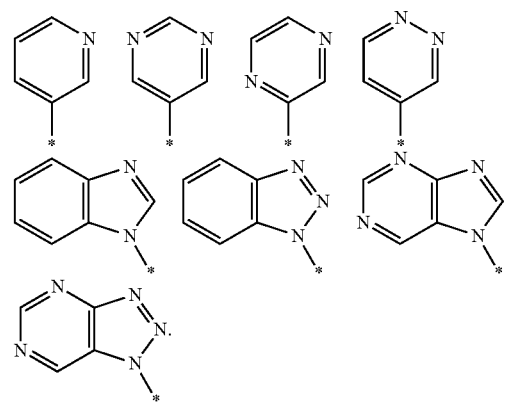

In one embodiment, the C ring substitution consists of the C13 methyl group.

In some embodiments, the compound is one of the following:

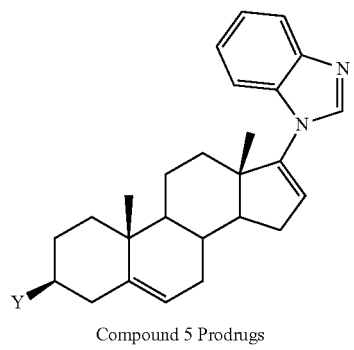

Compound 5 Prodrugs

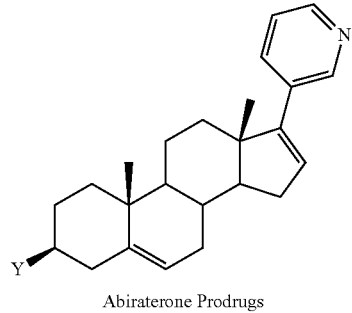

Abiraterone Prodrugs

The ability of compound 5 and abiraterone to inhibit CYP 17 and steroid 5a-reductases, the binding to and transactivation of androgen receptors, and the antiproliferative effects against two human prostate cancer cell lines, LNCaP and LAPC-4, were studied and reported in WO2006/093993 and in Potter et al. (Potter, G. A. et al., *J. Med. Chem.*, 1995, 38, 2463-2471). WO2006/093993 also reported the evaluation of the pharmacokinetics of Compounds 5 and 6 of Scheme 1 in mice and the in vivo antitumor activities against human LAPC-4 prostate carcinoma in mice.

In one embodiment, the prodrug of this invention includes a pharmaceutically-acceptable prodrug group. In some embodiments, the prodrug group is attached to the drug via one or more bonds that are labile under normal physiological conditions. In some embodiments, the prodrug group provides improved oral bioavailability and pharmacokinetics over the drug. In some embodiments, the prodrug group is incorporated at the Y position of a compound of Formula I.

In some embodiments, the compound of Formula I is:

benzyl or alkoxyalkyl, wherein each R group may or may not be joined to another R group to form a ring; and n is from 1-50, or a stereoisomer or pharmaceutically-acceptable salt thereof. In some embodiments, a value for n is selected for improved pharmacokinetic properties.

In some embodiments, the compound of Formula I is:

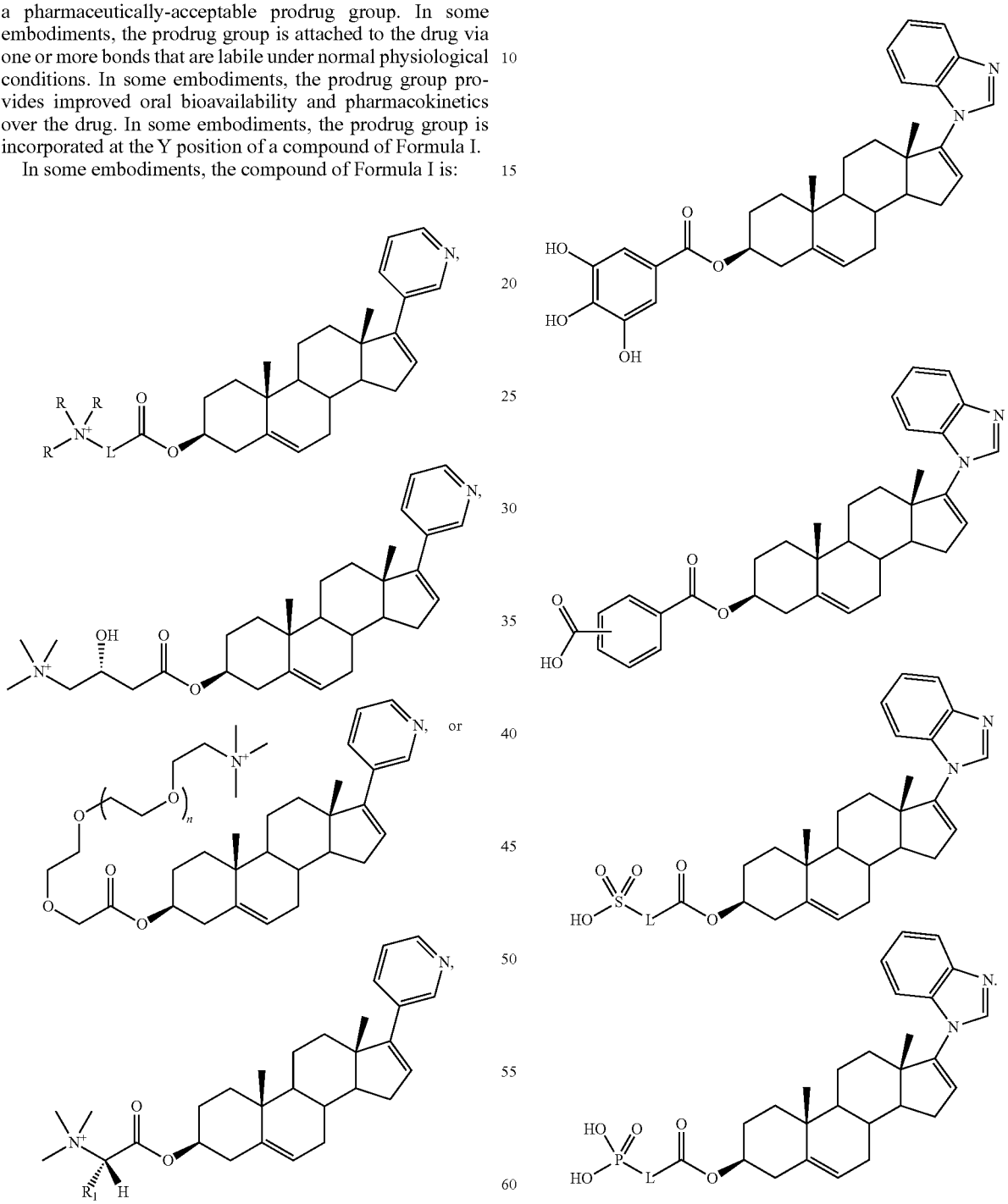

wherein $R_1$ is H, alkyl, alkylaryl, mercaptoalkyl, hydroxyalkyl, arylalkyl, alkylamino, aminoalkyl, alkylcarboxyl, carboxyalkyl, alkylamido, amidoalkyl, or other group derived from natural or unnatural amino acids; R is independently at each occurrence $C_1$-$C_5$-alkyl, hydroxyalkyl, phenyl, pyridyl, In some embodiments, the substitution of the prodrug group is modified to adjust the pKa of the prodrug. In some embodiments, the substitution of the prodrug group is modified to adjust the pKa of the prodrug such that the prodrug exists in a charged state at the desired point of adsorption, distribution, metabolism and/or excretion.

In some embodiments, the compound of Formula I is:

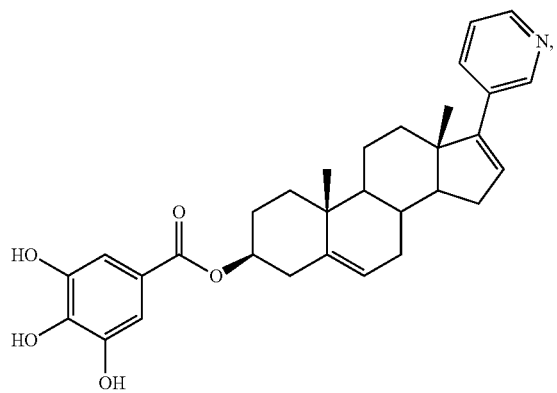

In some embodiments, the compound of Formula I is:

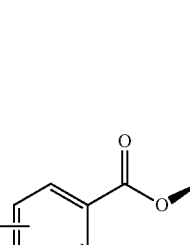

wherein n is from 0 to 50. In some embodiments, a value of n is chosen such that the pKa of the fluoroalkanol is within physiological range.

In some embodiments, the compound of Formula I is:

wherein n is from 0 to 50. In some embodiments, a value of n is chosen such that the pKa of the fluoroalkanol is within physiological range.

Some embodiments contemplate pharmaceutically-acceptable salts of the invention. Pharmaceutically-acceptable salts of the compounds of the invention are generated, for example, by treating the compounds of the invention with an acid, a hemi-acid, or a salt to afford the corresponding salt form. Non-limiting examples of pharmaceutically-acceptable salts include chlorides, bromides, iodides, phosphates, sulfates, carbonates, bicarbonates, formates, acetates, propionates, benzoates, picolinates, fumarates, maleates, malates, succinates, methanesulfonates, toluenesulfonates, mesitylenesulfonates, trifluoromethanesulfonates, tetrafluoroborates, tetraphenylborates, and hexafluorophosphates.

Exemplary Compound Preparation

The preparation of 17-benzazoles and 17-diazines is outlined herein, with these methods being applicable, analogously, to other analogs described herein.

The key intermediate in the synthesis of the 17-benzazole, 3β-acetoxy-17-chloro-16-formylandtrosta-5,16-diene (2), was obtained by the routine procedure as previously described (Njar, V. C. O. et al., *Bioorg. Med. Chem. Lett.*, 1996, 6, 2777-2782, and Njar, V. C. O. et al, *J. Med. Chem.*, 1998, 41, 902-912). Treatment of Compound 2 with benzimidazole in the presence of $K_2CO_3$ in DMF at approx. 80° C. gave the desired 3β-acetoxy-17-1H-benzimidazole (3) in near quantitative yield. Compound 3 was smoothly deformylated with 10% palladium on activated charcoal in N-meth-

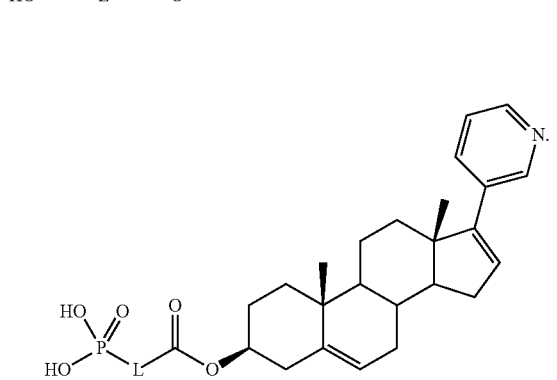

In some embodiments, the substitution of the prodrug group is modified to adjust the pKa of the prodrug. In some embodiments, the substitution of the prodrug group is modified to adjust the pKa of the prodrug such that the prodrug exists in a charged state at the desired point of adsorption, distribution, metabolism and/or excretion.

ylpyrrolidinone to give Compound 4 in 93% yield, from which hydrolysis gave the required 3β-hydroxy-17-benzimidazole (5):

the symmetrical 2H-1,2,3-triazole (7a) appeared as two pairs of doublets at δ 7.43, 7.45, 7.88 and 7.90, while the four aromatic protons of the unsymmetrical 1H-1,2,3-triazole (7b)

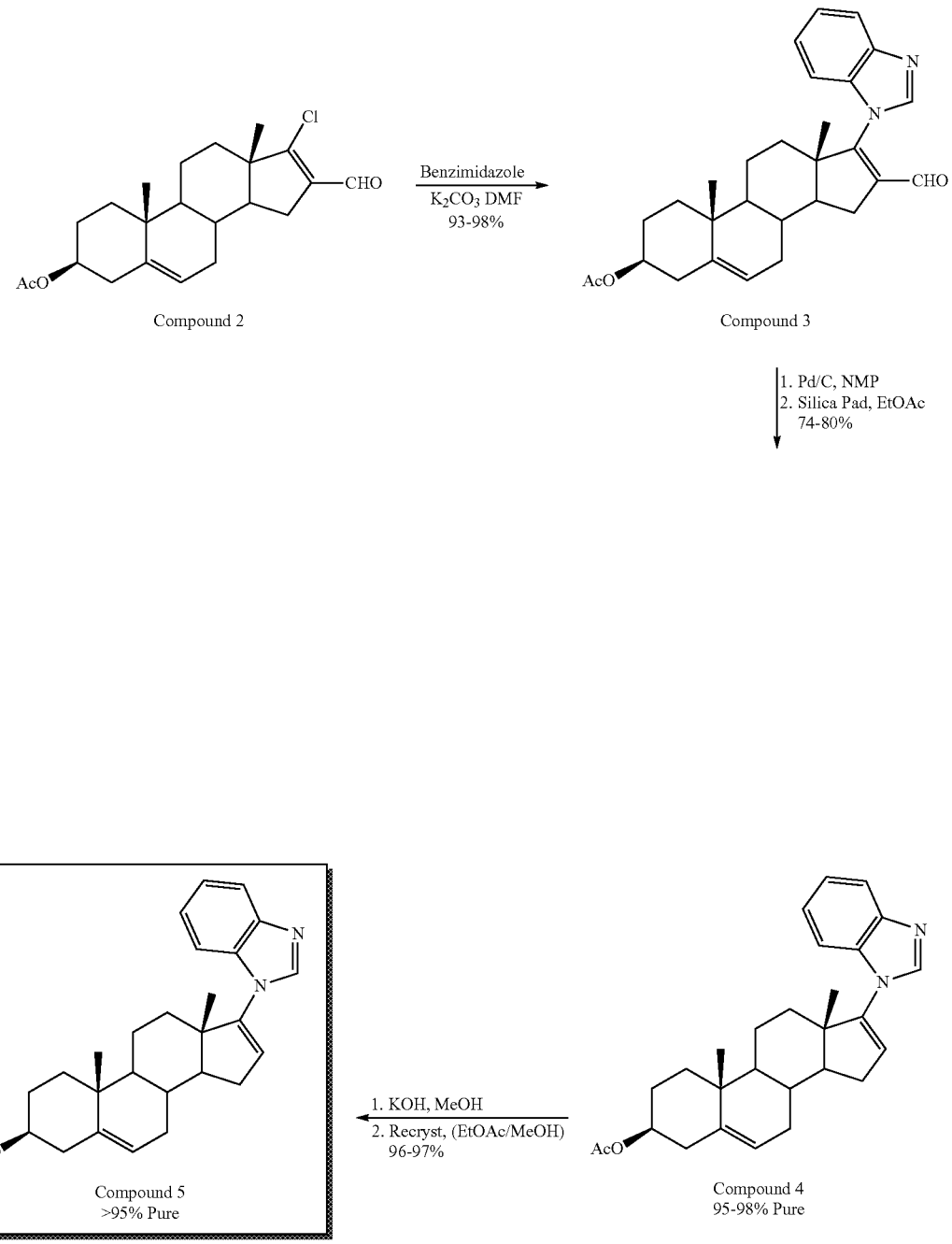

Modified Oppenauer oxidation of Compound 5 afforded the corresponding Δ$^4$-3-oxo analog (6).

The reaction of Compound 2 with benzotriazole in the presence of $K_2CO_3$ in DMF at approximately 80° C. gave the desired 3β-acetoxy-17-benzo-1H-1,2,3-triazole (7b) in excellent yield, together with the 2H-1,2,3-triazole regioisomer (7a) in approximately 5% yield. These two regioisomers were readily separated by flash column chromatography (FCC) on silica gel, and were easily identified by their respective proton NMR spectra. Thus, the four aromatic protons of appeared as a multiplet at δ 7.46 (2H) and doublets at δ 7.57 (1H) and 8.15 (1H), respectively. In addition, the 16-CHO proton in Compound 7a was significantly shifted downfield to δ 10.66 compared to that in Compound 7b at δ 9.59. Deformylation of Compound 7b with in situ generation of Rh(1,3-bis (diphenylphosphino)propane)$_2$$^+$Cl$^-$ catalyst [Rh(dppp)$_2$$^+$ Cl$^-$] in refluxing xylenes gave compound 8, and hydrolysis of the 3β-acetoxy group afforded the target 3β-hydroxy-17-(benzo-1H-1,2,3-triazol-1-yl)androsta-5,16-diene (9) in 90% yield.

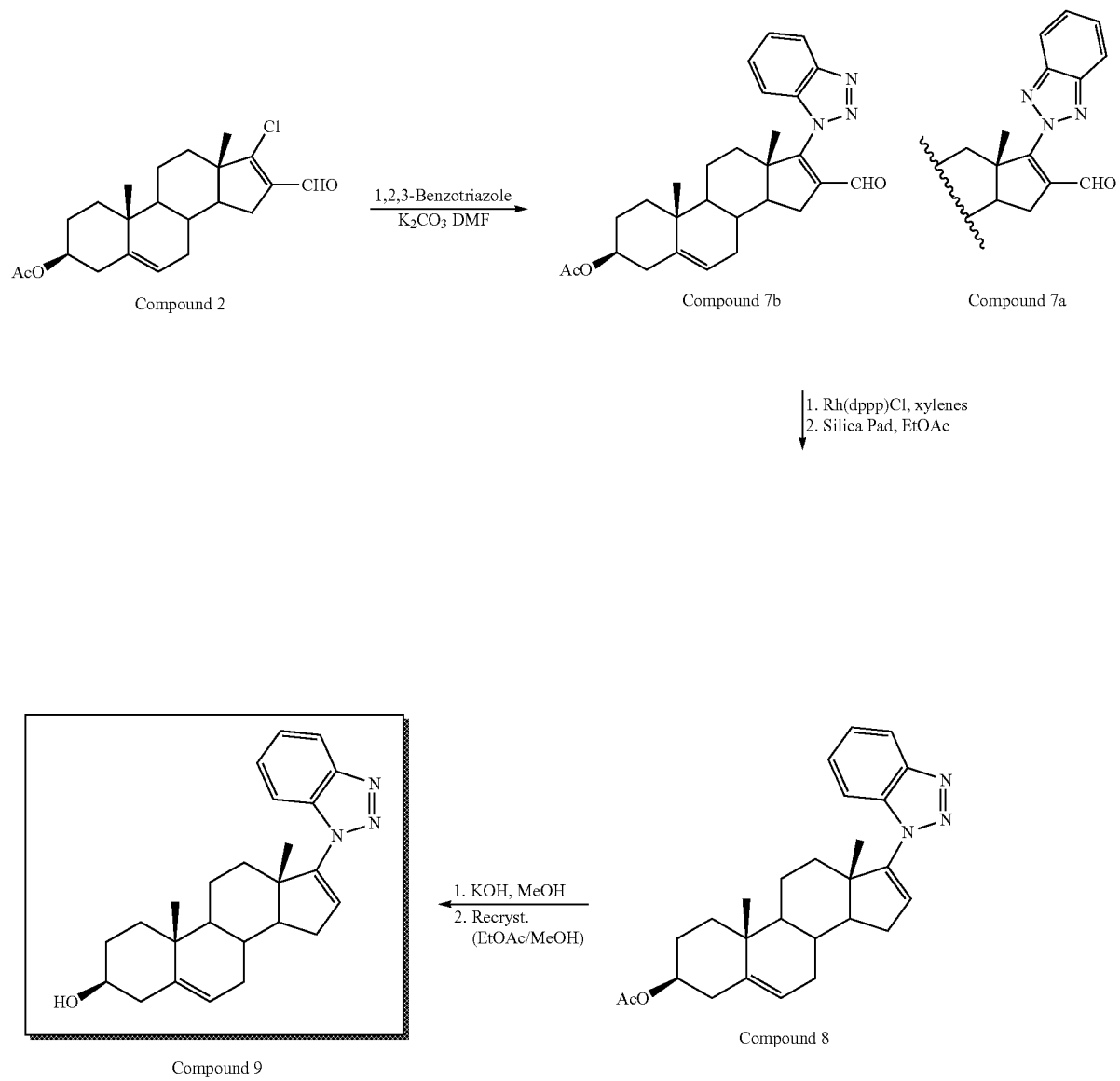

Synthesis of the 17-diazines, 17-diazine (14) and 17-pyrimidine (15), commenced from the readily-available dehydroepiandrosterone (Compound 11), which was converted to the corresponding 17-hydrazone (12) by treatment with hydrazine hydrate and hydrazine sulfate, as previously described by Potter et al. (Potter, G. A. et al., *Org. Prep. Proc. Int.*, 1997, 29, 123-1280). Treatment of Compound 12 with iodine in the presence of 1,1,3,3-tetramethylguanidine gave the vinyl 17-iodide (13) in excellent yield. The palladium-catalyzed cross-coupling reactions (Choshi, T. et al., *J. Org. Chem.*, 1995, 60, 5899-5904) of Compound 13 with (2-tributylstannyl)pyrazine or (5-tributylstannyl)pyrimidine proceeded to give 3β-hydroxy-17-(2-pyrazyl)-androsta-5,16-diene (14, 15%), and 3β-hydroxy-17-(5-pyrimidyl)-androsta-5,16-diene (15, 10%), respectively.

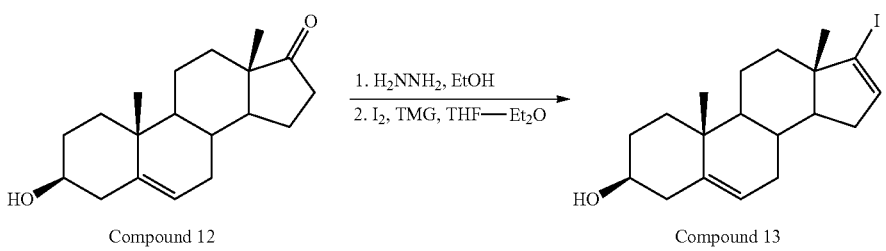

-continued

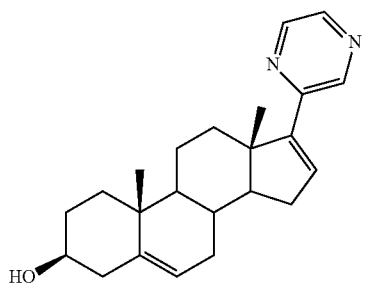

Compound 14

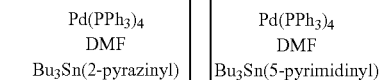

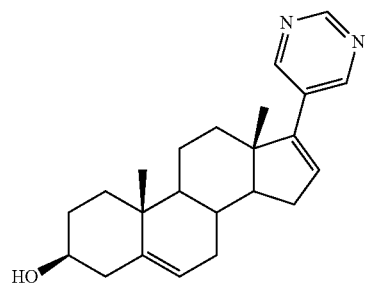

Compound 15

The identity of the target Compounds 14 and 15 were readily confirmed by their proton NMR spectra: the three nonequivalent protons of the 17-pyrazine moiety in Compound 14 appearing as three singlets at δ 8.35, 8.48 and 8.70, while the three protons of the 17-pyrimidine moiety in Compound 15 appearing as two singlets at δ 8.73 (2H) and δ 9.07 (1H). Further, the 17-diazine groups of Compounds 14 and 15 exhibit different influences on the chemical shifts of the corresponding 16-olefinic protons with respect to that of the precursor $\Delta^{16}$-17-iodide 13: the 16-H in Compound 14 appearing as a singlet at δ 6.77, being significantly deshielded compared to the 16-H in Compound 13 (δ 6.14); and the 16-H in Compound 15 appearing at δ 6.11, similar to Compound 13. Compound 15 has been reported previously by Haidar et al (Haidar, S. et al., *Arch. Pharm. Med. Chem.*, 2001, 334, 373-374) and its biological and pharmacological activities have also been described (Haidar, S. et al., *J. Steroid Biochem. Molec. Biol.*, 2003, 84, 555-562).

Abiraterone may be prepared as described in the literature (Potter, G. A. et al., *J. Med. Chem.*, op. cit.).

Synthesis of the disclosed prodrugs is illustrated herein, with the understanding that the examples provided can be applied to all compounds contemplated by the instant disclosure.

The present invention also provides pharmaceutical compositions comprising a pharmaceutically-acceptable carrier and one or more of the compounds disclosed herein. Suitable pharmaceutically-acceptable carriers include, for example, vehicles, adjuvants, excipients, and diluents.

The present invention also provides methods of treating urogenital and/or androgen-related cancers, diseases and/or conditions, including, without limitation, breast cancer, prostate cancer (e.g., prostatic adenocarcinoma), other urogenital cancers, prostate hyperplasia (BPH), and/or other androgen-related diseases and/or conditions, by administering to a subject in need or want thereof a therapeutically-effective amount of a compound of the present invention. The treatment may be prophylactic (referring to any degree of inhibition of the onset of a cellular disorder, including complete inhibition, such as in a subject expected to soon exhibit the cellular disorder) or therapeutic (referring to any degree of inhibition or any degree of beneficial effects on the disorder or condition in the subject (e.g., human), (e.g., inhibition of the growth or metastasis of a tumor or circulating tumor cells). Maintenance therapy, in which continued suppression of symptoms or progression of disease is achieved by continued administration of the compound, is also contemplated by this invention. Examples of prostate diseases that can be treated include, e.g., prostatic hyperplasia (BPH), and prostate cancer (e.g., prostatic adenocarcinoma).

Non-limiting examples of cancer symptoms include: tumors, persistent cough, bloody saliva, changes in bowel habits, bloody stool, anemia, lumps including lumps of the breast or testicle, bodily discharges, changes in urinary habits, pain or burning upon urination, prostate enlargement, bloody urine, swollen glands, warts, moles, genital bleeding, involuntary weight gain or loss, persistent itching, persistent skin discoloration, non-healing sores, headaches, pain or discomfort such as in the back or pelvis, cramps such as abdominal cramps, weakness, and loss of appetite.

Methods of administering a compound of the present invention to a subject, for example, a mammal, such as a rat, rabbit, dog or human, are known in the art. Although more than one route may be used to administer a particular composition, a particular route can provide a more immediate and more effective result than another route.

In some embodiments, a pharmaceutical composition is formulated for oral administration. In some embodiments, the composition comprises a suspension of a compound in a suitable vehicle. Non-limiting examples of vehicles for oral administration include phosphate-buffered saline (PBS), 5% dextrose in water (D5W), 1% carboxymethyl cellulose (CMC) and a syrup. In some embodiments, a composition is formulated to stabilize the consistency of a dose over a period of storage and administration. In some embodiments, the composition comprises a solution. In some embodiments, a solution comprises an effective amount of one or more compounds dissolved in a diluent. Non-limiting examples of diluents include water, saline, and buffers. In some embodiments, the composition comprises a solid dosage form. In some embodiments, the solid dosage form comprises a capsule, a caplet, a lozenge, a sachet, or a tablet. In some embodiments, the solid dosage form is a liquid-filled dosage form. In some embodiments, the solid dosage form is a solid-filled dosage form. In some embodiments, the solid dosage form is a solid-filled tablet, capsule, or caplet. In some embodiments, the solid-filled dosage form is a powder-filled dosage form. In some embodiments, the solid dosage form comprises a compound in the form of micronized particles, solids or granules. In some embodiments, the composition comprises an emulsion. In some embodiments, the emulsion comprises a compound of the invention characterized by surfactant properties.

In some embodiments, the solid dosage form comprises one or more of lactose, sorbitol, maltitol, mannitol, cornstarch, potato starch, microcrystalline cellulose, hydroxypropyl cellulose, acacia, gelatin, colloidal silicon dioxide, croscarmellose sodium, talc, magnesium stearate, stearic acid, pharmaceutically-acceptable excipients, colorants, diluents, buffering agents, moistening agents, preservatives, flavoring agents, carriers, and binders. In some embodiments, the solid dosage form comprises one or more materials that facilitate manufacturing, processing or stability of the solid dosage form. In some embodiments, a lozenge comprises a flavoring agent. Non-limiting examples of excipients useful in the present invention include sucrose, gum acacia, gum tragacanth, a pastille, an inert base, a gelatin, glycerin, a sucrose emulsion, an acacia emulsion, and a gel. In some embodiments, a solid dosage form is coated. In some embodiments, the coating improves absorption of the compound in the gastrointestinal tract. Non-limiting examples of coatings include cellulose acetate phthalate (CAP), polyvinyl acetate phthalate (CVAP), and modified coatings thereof.

In some embodiments, the composition is formulated as an aerosol. In some embodiments, the aerosol is administered via inhalation. In some embodiments, the aerosol comprises one or more propellants. Non-limiting examples of propellants include dichlorodifluoromethane, hydrofluorocarbon (such as HFC 134a and/or 227), and nitrogen.

In some embodiments, a compound is administered by a route that is oral, parenteral, enteral, intraperitoneal, topical, transdermal, ophthalmic, nasal, local, non-oral, aerosol, spray, inhalation, subcutaneous, intravenous, intramuscular, buccal, sublingual, rectal, vaginal, intra-arterial, or intrathecal. In some embodiments, a dose is administered by a route that is oral, parenteral, enteral, intraperitoneal, topical, transdermal, ophthalmic, nasal, local, non-oral, aerosol, spray, inhalation, subcutaneous, intravenous, intramuscular, buccal, sublingual, rectal, vaginal, intra-arterial, or intrathecal. In some embodiments, the compound is administered as a suspension in PBS, D5W, or a carbohydrate-based syrup.

In some embodiments, the dose is administered as a suspension in PBS, D5W, or a carbohydrate-based syrup.

In some embodiments, a dose administered to a subject is an effective dose. In some embodiments, the effective dose provides a therapeutic response in the subject within a therapeutically-useful time frame. In some embodiments, the effective dose comprises a therapeutically-effective amount of a compound. In some embodiments, the therapeutically-effective amount provides a therapeutic response in the subject within a therapeutically-useful time frame. The specific dose level and frequency of dosage are influenced by a variety of factors, including the activity, metabolic stability, bioavailability, rate of excretion, biological half-life, and mode and time of administration of the compound; the age, body weight, health condition, gender, diet, and physical and health characteristics of the subject; and the severity of the cancer or other disease or condition.

Any effective amount of the compound may be administered. In some embodiments, a dose comprises an effective amount of a compound. In some embodiments, a dose is administered once a day. In some embodiments, a dose is administered more than once a day. In some embodiments, a dose is greater than about 1 mg/day. In some embodiments, a dose is greater than about 5 mg/day. In some embodiments, a dose is greater than about 10 mg/day. In some embodiments, a dose is greater than about 25 mg/day. In some embodiments, a dose is greater than about 50 mg/day. In some embodiments, a dose is greater than about 100 mg/day. In some embodiments, a dose is less than about 5000 mg/day. In some embodiments, a dose is less than about 4000 mg/day. In some embodiments, a dose is less than about 3000 mg/day. In some embodiments, a dose is less than about 2500 mg/day. In some embodiments, a dose is less than about 2000 mg/day. In some embodiments, a dose is less than about 1500 mg/day. In some embodiments, a dose is less than about 1000 mg/day. In some embodiments, a dose is less than about 500 mg/day. In some embodiments, a dose is from about 500 mg to about 1200 mg per day. In some embodiments, a dose is from about 500 mg to about 1500 mg per day. In some embodiments, a dose is from about 1 mg to about 5000 mg per day. In some embodiments, a dose is from about 5 mg to about 4000 mg per day. In some embodiments, a dose is from about 10 mg to about 3000 mg per day. In some embodiments, a dose is from about 25 mg to about 2000 mg per day. In some embodiments, a dose is from about 50 mg to about 2500 mg per day. In some embodiments, a dose is from about 100 mg to about 2000 mg per day. In some embodiments, a dose is from about 100 mg to about 1000 mg per day. In some embodiments, a dose is from about 100 mg to about 500 mg per day.

In one embodiment, a dose is about 0.01 to about 100 mg/kg of subject body mass per day. In some embodiments, a dose is about 0.05 to about 50 mg/kg of subject body mass per day. In some embodiments, a dose is about 0.1 to about 40 mg/kg of subject body mass per day. In some embodiments, a dose is about 0.25 to about 30 mg/kg of subject body mass per day. In some embodiments, a dose is about 0.5 to about 20 mg/kg of subject body mass per day. In some embodiments, a dose is about 0.75 to about 15 mg/kg of subject body mass per day. In some embodiments, a dose is about 1 to about 10 mg/kg of subject body mass per day. In some embodiments, a dose is about 2 to about 5 mg/kg of subject body mass per day.

In some embodiments, a composition has a concentration of greater than about 0.01% of the compound by mass. In some embodiments, a composition has a concentration of greater than about 0.025% of the compound by mass. In some embodiments, a composition has a concentration of greater than about 0.05% of the compound by mass. In some embodiments, a composition has a concentration of greater than about 0.075% of the compound by mass. In some embodiments, a composition has a concentration of greater than about 0.1% of the compound by mass. In some embodiments, a composition has a concentration of less than about 25% of the compound by mass. In some embodiments, a composition has a concentration of less than about 20% of the compound by mass. In some embodiments, a composition has a concentration of less than about 15% of the compound by mass. In some embodiments, a composition has a concentration of less than about 10% of the compound by mass. In some embodiments, a composition has a concentration of less than about 7.5% of the compound by mass. In some embodiments, a composition has a concentration of less than about 5% of the compound by mass. In some embodiments, a composition has a concentration of less than about 3% of the compound by mass. In some embodiments, a composition has a concentration of about 0.01% to about 25% of the compound by mass. In some embodiments, a composition has a concentration of about 0.025% to about 20% of the compound by mass. In some embodiments, a composition has a concentration of about 0.05% to about 15% of the compound by mass. In some embodiments, a composition has a concentration of about 0.02% to about 5% of the compound by mass. In some embodiments, a composition has a concentration of about 0.1% to about 3% of the compound by mass. In some embodiments, a composition has a concentration of about 10% to about 80% of the compound by mass.

In some embodiments, a compound of the invention is administered alone. In some embodiments, a compound is administered with one or more other ingredient(s), for example, a pharmaceutically-acceptable excipient, carrier or diluent. In some embodiments, a compound is used in combination with other cancer treatments. In some embodiments, the compounds of this invention are used as a part of or in combination with known cancer treatments, for example, hormone therapy, chemotherapy, radiation therapy, immunotherapy, and/or surgery. In one embodiment, one or more compounds are used in combination with one or more additional agents. In some embodiments, the additional agent is a drug. In some embodiments, the additional agent is a hormone. Non-limiting examples of drugs and/or hormones for use in combination with the prodrugs of this invention include anti-androgens such as flutamide and nilutamide; another CYP 17 inhibitor, such as abiraterone; luteinizing hormone-releasing hormone agonists, such as leuprolide, goserelin and buserelin; and drugs that prevent the adrenal glands from making androgens, such as ketoconazole and aminoglutethimide; and estrogens. Non-limiting examples of cancer drugs include cyclophosphamide, methotrexate, 5-fluorouracil (5-FU), doxorubicin, carboplatin, carmustine, chlorambucil, cisplatin, cyclophosphamide, dacarbazine, ifosfamide, mechlorethamin, melphalan, procarbazine, bleomycin, doxorubicin, idarubicin mitoxantrone, chlorodeoxyadenosine, cytarabine, fludarabine, 6-mercaptopurine, methotrexate, 6-thioguanine, pentostatin, etoposide, gemcitabine, steroid creams, corticosteroids, prednisone, and dexamethasone.

Compounds of this invention may be administered to a subject at any time, as determined by the treating physician. In some embodiments, the compound is administered during one or more of Stage II, Stage III, and Stage IV of the cancer. In some embodiments, the compound is administered during an advanced stage of a urogenital and/or androgen-related disease or condition.

The embodiments of the disclosure are provided for the purpose of illustration, not limitation.

In some embodiments, the invention provides compound of Formula I:

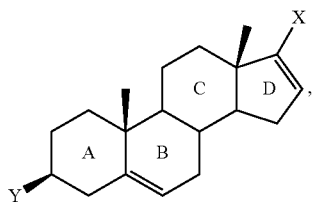

Formula I wherein:
the ABC ring structure is optionally substituted independently at each position and wherein hydrogen substituents on adjacent carbon atoms of the ABC ring structure are optionally removed and replaced by a pi-bond between the adjacent carbon atoms;
Y is Z-L-C(=O)O—; and
either
X is an optionally substituted heterocycle that is a pyridine, pyrazine, pyrimidine, pyridazine, benzimidazole, benzotriazole, pyrimidinoimidazole, or pyrimidinotriazole group, wherein the benzimidazole, benzotriazole, pyrimidinoimidazole or pyrimidinotriazole group is bonded to the C17 position through a nitrogen atom on a 5-membered ring of the heterocycle, and the pyridine, pyrazine, pyrimidine, or pyridazine group is bonded to the C17 position through a carbon atom of the heterocycle;
L is $C_1$-$C_{12}$-alkyl, fluoro-$C_2$-$C_6$-alkyl, aryl, arylalkyl, alkylaryl, alkoxyalkyl, polyalkoxyalkyl, or heteroaryl, any of which is optionally cyclic or together with Z forms a ring, wherein L is optionally substituted with one or more of alkyl, arylalkyl, alkylaryl, alkylheteroaryl, halogen, hydroxyl, alkoxy, alkylamino, and mercaptan; and
Z is a charged group that is charged under normal physiological conditions, wherein the charged group is a quaternary ammonium group of the formula $(R_3N^+)$—, wherein each R group is independently $C_1$-$C_7$-branched alkyl, $C_1$-$C_7$-straight-chain alkyl, aryl, alkylaryl, aralkyl, heteroaryl, or two or more R groups together form a ring; a sulfonic acid; a phosphonic acid; a fluoroalkanol; or an acidic hydroxyl group,
or a pharmaceutically-acceptable salt thereof.
or
X is an optionally-substituted pyridine group;
L is $C_1$-$C_{12}$-alkyl, fluoro-$C_2$-$C_6$-alkyl, aryl, arylalkyl, alkylaryl, alkoxyalkyl, polyalkoxyalkyl, or heteroaryl, any of which is optionally cyclic or together with Z forms a ring, wherein L is optionally substituted with one or more of alkyl, arylalkyl, alkylaryl, alkylheteroaryl, halogen, hydroxyl, alkoxy, alkylamino, and mercaptan; and
Z is a charged group that is charged under normal physiological conditions, wherein the charged group is a quaternary ammonium group of the formula $(R_3N^+)$—, wherein each R group is independently $C_1$-$C_7$-branched alkyl, $C_1$-$C_7$-straight-chain alkyl, aryl, alkylaryl, aralkyl, heteroaryl, or two or more R groups together form a ring; a sulfonic acid; a phosphonic acid; a fluoroalkanol; or an acidic hydroxyl group,
or a pharmaceutically-acceptable salt thereof.

In some embodiments, X is optionally substituted with one or more of halogen, amino, aminoalkylene, hydroxy, —SH, —S—$C_1$-$C_6$-alkyl, $C_1$-$C_6$-alkyl and halogenated $C_1$-$C_6$-alkyl.

In some embodiments, the pyridine, pyrazine, pyrimidine, pyridazine, benzimidazole, benzotriazole, pyrimidinoimidazole, and pyrimidinotriazole groups are, respectively:

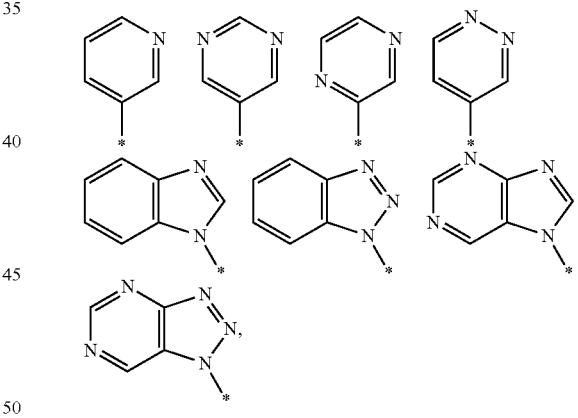

wherein each * indicates a point of attachment to the C17 position.

In some embodiments, the ABC ring structure is optionally substituted with one or more of $C_1$-$C_6$-alkyl, halogenated $C_1$-$C_6$-alkyl, $C_1$-$C_6$-alkenyl, halogenated $C_1$-$C_6$-alkenyl, halogen, amino, aminoalkylene, hydroxyimino, and hydroxyl.

In some embodiments, Z is a quaternary ammonium group, wherein the quaternary ammonium group is trimethyl ammonium, triethyl ammonium, triphenyl ammonium, benzyldimethyl ammonium, benzyldiethyl ammonium, N-methylpiperidinium, N-ethylpiperidinium, or tribenzyl ammonium.

In some embodiments, Z is a sulfonic acid, and L is $C_1$-$C_6$-alkyl.

In some embodiments, Z is a phosphonic acid, and L is $C_1$-$C_6$-alkyl.

In some embodiments, the compound is:

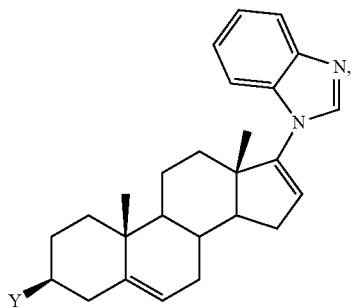

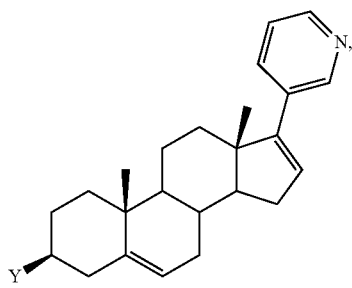

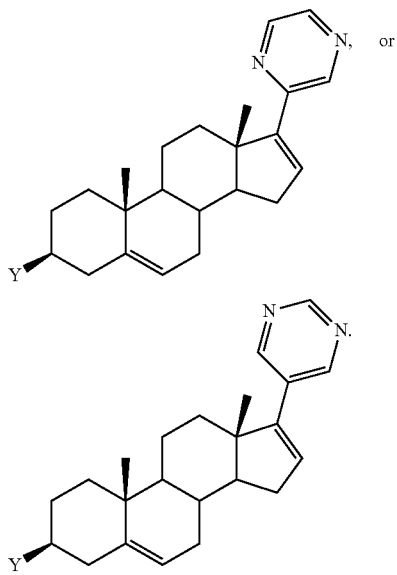

In some embodiments, the compound is:

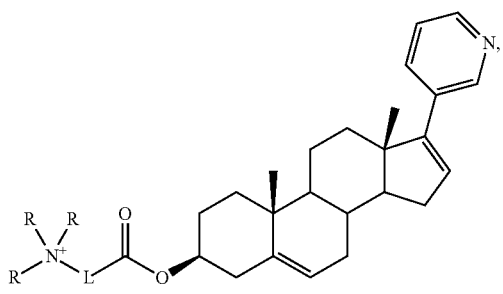

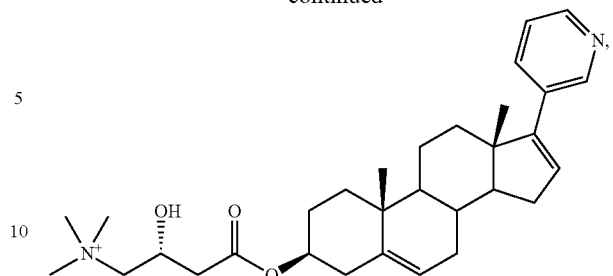

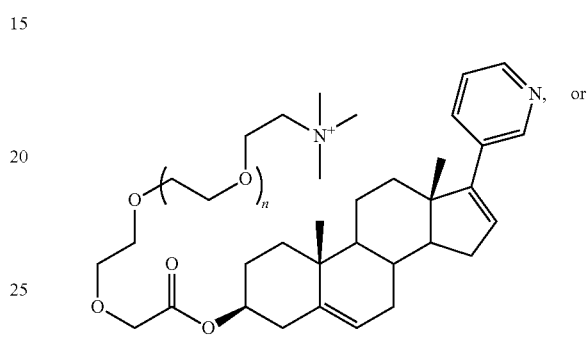

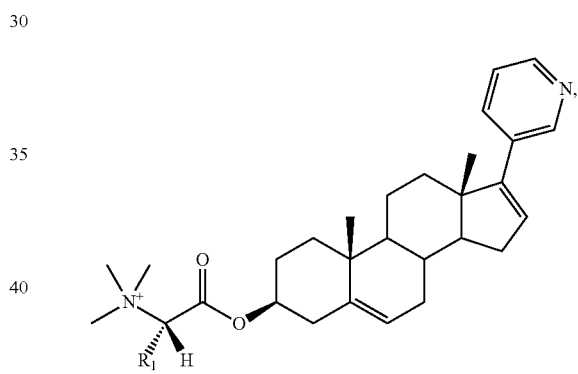

wherein R is $C_1$-$C_6$-alkyl, aryl, heteroaryl, arylalkyl, or alkylaryl; $R_1$ is $C_1$-$C_8$-alkyl, aryl, aralkyl, alkylaryl, or alkylheteroaryl; and n is from 1 to 49.

In some embodiments, the invention provides a pharmaceutical composition comprising a therapeutically-effective amount of one or more compounds of the invention and one or more pharmaceutically-acceptable excipients, bulking agents, binders, flow agents, release agents, carriers or diluents.

In some embodiments, the composition is an oral dosage form.

In some embodiments, the oral dosage form is a tablet, a caplet, a capsule or a liquid suspension.

In some embodiments, the amount of the compound is less than about 1000 mg. In some embodiments, the amount of the compound is less than about 2000 mg.

In some embodiments, the amount of the compound is from about 100 mg to about 500 mg. In some embodiments, the amount of the compound is from about 500 mg to about 1500 mg.

In some embodiments, the compound is:

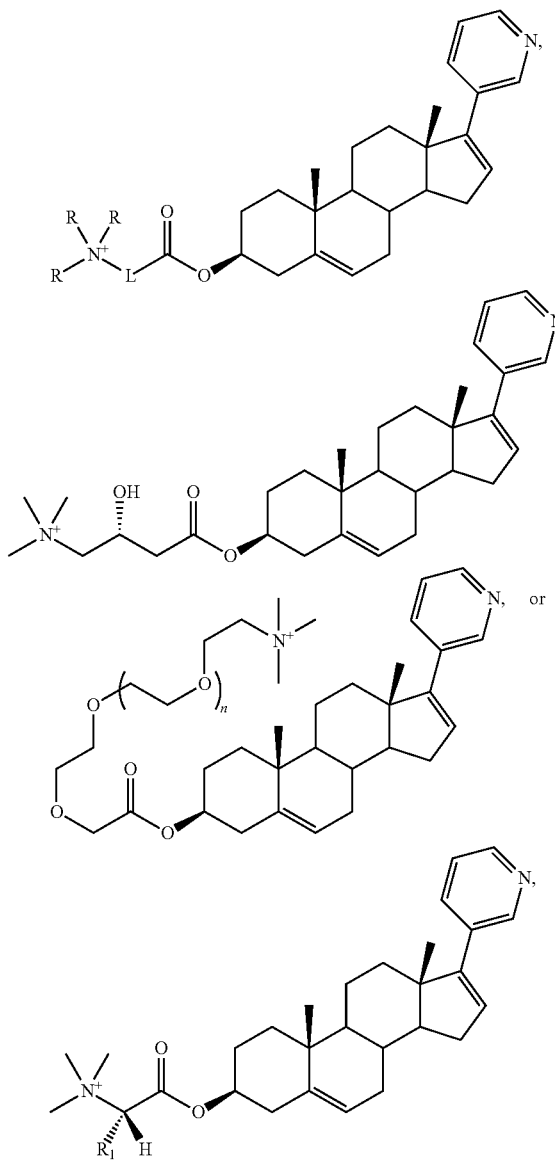

wherein R is $C_1$-$C_6$-alkyl, aryl, heteroaryl, arylalkyl, or alkylaryl; and $R_1$ is $C_1$-$C_8$-alkyl, aryl, aralkyl, alkylaryl, or alkylheteroaryl; and n is from 1 to 49.

In some embodiments, the invention provides a method of treating a cancer or a urogenital disease in a subject in need or want thereof, the method comprising administering to the subject a therapeutically-effective amount of a compound of the invention.

In some embodiments, the cancer is a urogenital and/or androgen-related cancer.

In some embodiments, the cancer or urogenital disease is prostate cancer, breast cancer, ovarian cancer, other urogenital cancer, or prostate hyperplasia.

In some embodiments, the method further comprises administering to the subject a therapeutically-effective amount of one or more of an anti-androgen, a CYP17 inhibitor, a luteinizing hormone-releasing hormone agonist, a drug for preventing androgen production, an estrogen, and a chemotherapy drug.

In some embodiments, the amount is less than about 1000 mg. In some embodiments, the amount is less than about 2000 mg.

In some embodiments, the amount is from about 100 to about 500 mg. In some embodiments, the amount is from about 500 to about 1500 mg.

In some embodiments, the compound is:

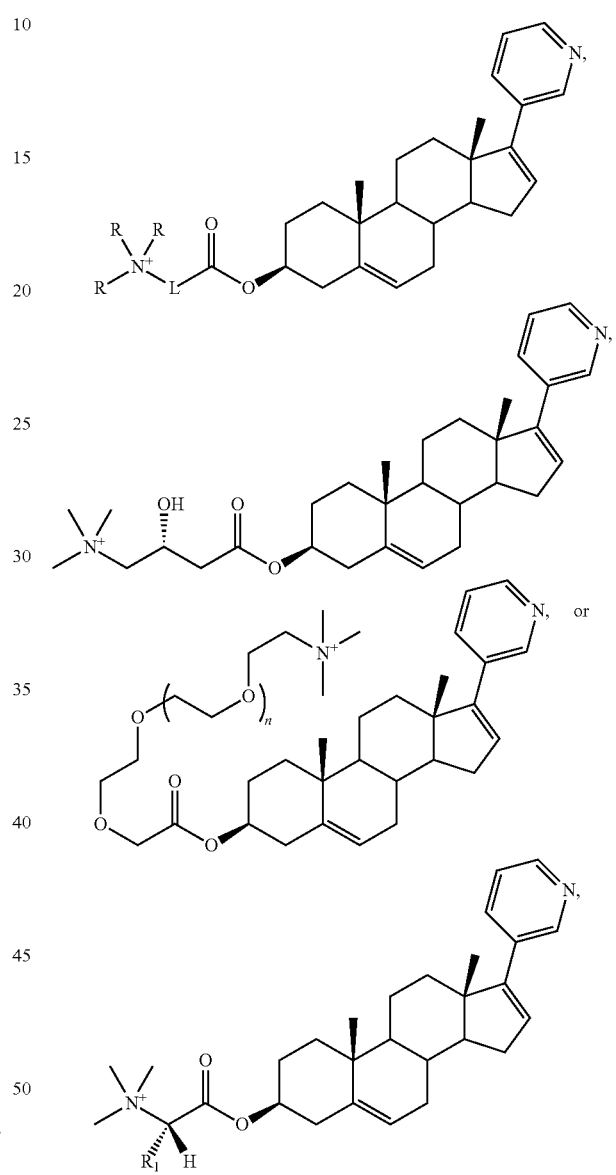

wherein R is $C_1$-$C_6$-alkyl, aryl, heteroaryl, arylalkyl, or alkylaryl; and $R_1$ is $C_1$-$C_8$-alkyl, aryl, aralkyl, alkylaryl, or alkylheteroaryl; and n is from 1 to 49.

In some embodiments, the invention provides a method of treating a cancer or a urogenital disease in a subject in need or want thereof, the method comprising administering to the subject a therapeutically-effective amount of a compound of the invention, in combination with a hormone therapy, a chemotherapy, a radiation therapy, an immunotherapy, or surgery.

In some embodiments, the cancer comprises a urogenital and/or androgen-related cancer.

In some embodiments, the cancer or urogenital disease is prostate cancer, breast cancer, ovarian cancer, other urogenital cancer, or prostate hyperplasia.

In some embodiments, the amount is less than about 1000 mg. In some embodiments, the amount is less than about 2000 mg.

In some embodiments, the amount is from about 100 to about 500 mg. In some embodiments, the amount is from about 500 to about 1500 mg.

In some embodiments, the compound is:

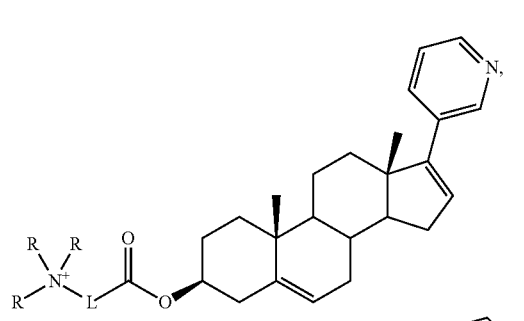

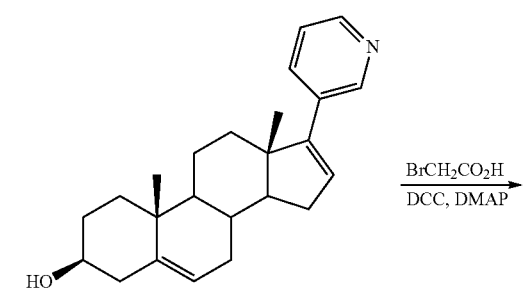

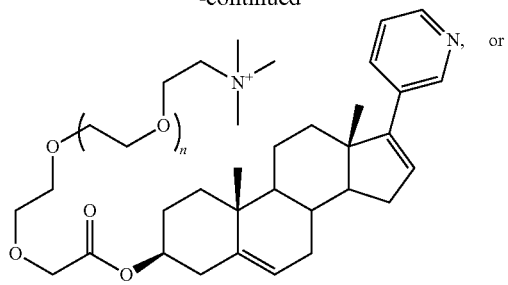

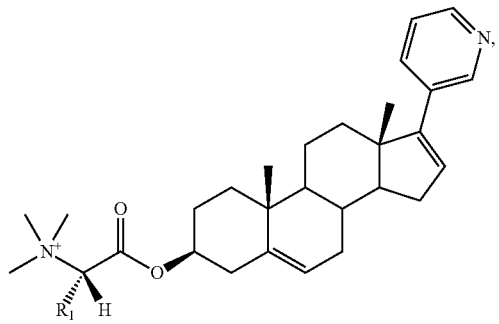

wherein R is $C_1$-$C_6$-alkyl, aryl, heteroaryl, arylalkyl, or alkylaryl; and $R_1$ is $C_1$-$C_8$-alkyl, aryl, aralkyl, alkylaryl, or alkylheteroaryl; and n is from 1 to 49.

EXAMPLES

Example 1

Betaine Ester of Abiraterone

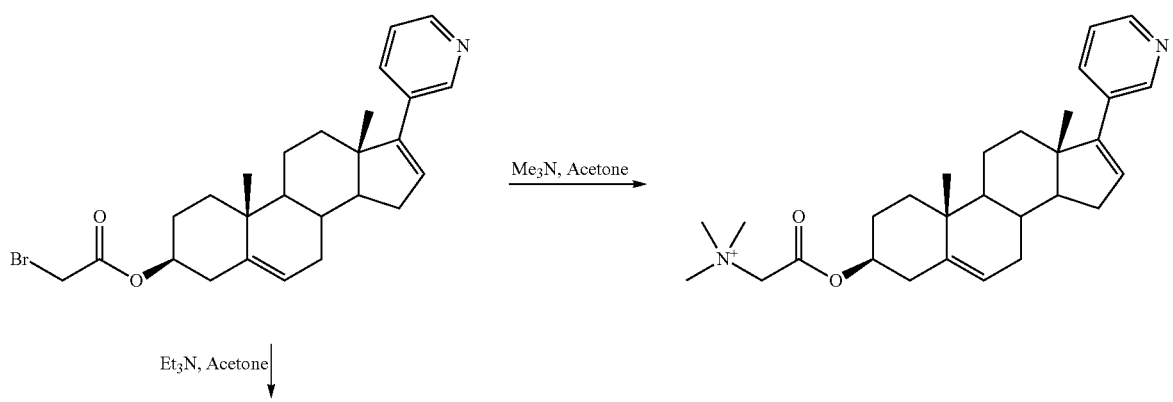

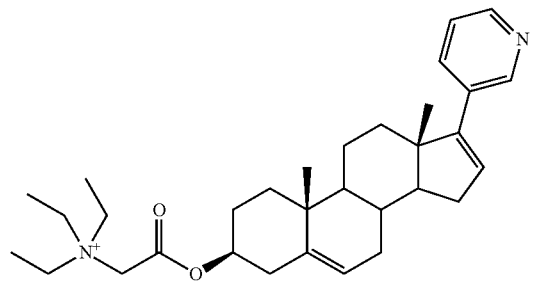

A solution of bromoacetic acid (3.0 mmol 417 mg) in dichloromethane (10 mL) is stirred while dicyclohexylcarbodiimide (3.0 mmol, 619 mg), dimethylaminopyridine (0.5 mmol, 61 mg), followed by a solution of abiraterone (2.9 mmol, 1.08 g) in dichloromethane (3 mL) are added. The resultant mixture is stirred at room temperature for four hours. The mixture is filtered to remove precipitated dicyclohexyl urea, and poured into ethyl acetate. The organic layers are washed (1N HCL, 5% sat'd NaHCO$_3$), dried (brine, MgSO$_4$), and concentrated, with purification by column chromatography affording the pure alpha-halo ester.

The above-prepared bromoester (1.5 mmol, 743 mg) is dissolved in acetone (10 mL) and triethylamine (2.5 mmol, 253 mg, 350 µL) is added. The mixture is stirred until the steroid starting material is shown to be exhausted by TLC. The reaction mixture is concentrated in vacuo, and the residue is purified by reversed-phase HPLC to afford pure triethylammonium acetate of abiraterone.

Alternately, the above prepared bromoester (1.5 mmol, 743 mg) is dissolved in acetone (10 mL) and trimethylamine (2.5 mmol, 148 mg, 232 µL) is added. The mixture is stirred until the steroid starting material is shown to be exhausted by TLC, then concentrated in vacuo, and the residue is purified by reversed-phase HPLC to afford pure trimethylammonium acetate of abiraterone.

Example 2

Carnitine Ester of Abiraterone

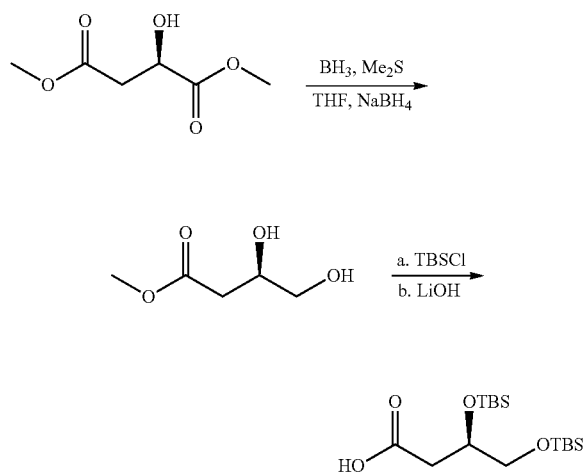

A solution of R-dimethylmalate (10 mmol, 1.62 g) in THF (40 mL) is cooled at −78° C. and stirred while borane-dimethylsulfide complex (9.5 mmol, 4.75 mL of a 2.0M solution) in THF is added. The mixture is allowed to warm to room temperature and stirred while heating at reflux until exhaustion of the starting diester is indicated by TLC. The reaction mixture is quenched by slow addition of THF-water (1:1, 10 mL), and the resulting mixture is carefully poured into a solution of sodium hydroxide (5M, 10 mL), and stirred overnight. The reaction mixture is concentrated in vacuo, and the residue is taken up into ethyl acetate (50 mL). The organic layer is washed (1N, HCl, 5% sat'd aq NaHCO$_3$), dried (brine, MgSO$_4$), and concentrated in vacuo, with the residue being distilled in vacuo to afford purified methyl R-3,4-dihydroxybutyrate, or the residue may be used directly in the following step.

A solution of methyl R-3,4-dihydroxybutryate (6 mmol, 804 mg) in dry DMF (12 mL) is stirred at room temperature while tert-butyldimethylsilyl chloride (13.2 mmol, 996 mg) and imidazole (16 mmol, 545 mg) are added alternately in portions. The resultant mixture is stirred at room temperature for three hours, and is poured into a mixture of ethyl acetate (100 mL) and water. The aqueous phase is separated, and extracted with ethyl acetate (50 mL), and the combined organics are dried (brine, MgSO$_4$), filtered and concentrated in vacuo to afford the crude bis-silyloxy ester. Distillation in vacuo using a kugelrohr oven affords the pure methyl R-3,4-bis(tert-butyldimethylsiloxy)butyrate.

The above-prepared protected ester (5 mmol, 1.81 g) is dissolved in THF:water (4:1, 20 mL) and a solution of lithium hydroxide (10 mmol, 239 mg) in water (4 mL) is added. The reaction mixture is stirred until the ester is exhausted, as indicated by TLC, and poured into water, before the pH is adjusted to <5 with HCl. The mixture is extracted with ethyl acetate (3×50 mL) and the combined organics are dried (brine, MgSO$_4$), and concentrated in vacuo to afford the crude acid, which is purified by reversed-phase HPLC, or column chromatography to afford the desired R-3,4-bis(tert-butyldimethylsilyloxy)butyric acid.

The protected acid is used in the preparation of an abiraterone prodrug.

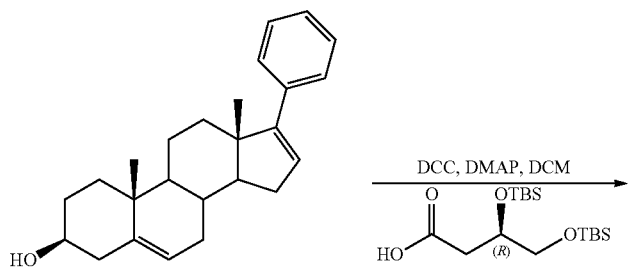
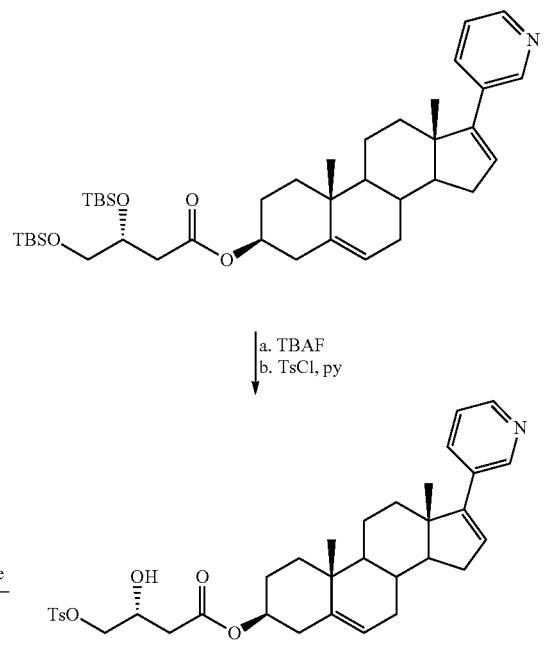

A solution of R-3,4-bis(tert-butyldimethylsilyloxy)butyric acid (1.0 mmol, 349 mmol), abiraterone (1.0 mmol, 374 mg) in dichloromethane (10 mL) is treated with EDC-HCl (1.0 mmol, 192 mg) and DMAP (0.1 mmol, 12 mg). The resultant mixture is stirred at room temperature for three hours, then poured into 1N HCl. The aqueous phase is separated, washed with dichloromethane (3×20 mL), and the combined organics are washed (3×50 mL 1N HCl, 1×50 mL 5% aq. NaHCO$_3$), dried (brine, MgSO$_4$), and concentrated, with the residue being purified by flash column chromatography (silica, EtOAc/hexanes elution) to afford the desired bis-protected ester.

The bis-silyl protected ester (0.5 mmol, 358 mg) is dissolved in THF (5 mL) and a solution of TBAF (1.0M in THF, 1.1 mL) is added. The solution is stirred for 2.5 hours, and is poured into water (10 mL). The aqueous phase is extracted with EtOAc (3×20 mL) and the combined organics are dried (brine, MgSO$_4$) and concentrated in vacuo, with the residue being purified by flash column chromatography (silica, EtOAc/hexanes elution) to afford the desired dihydroxy ester.

A solution of the R-3,4-dihydroxybutryl ester of abiraterone (0.5 mmol, 238 mg) in pyridine is treated with toluenesulfonyl chloride (0.5 mmol, 95 mg) and stirred for 24 hours at 4° C. The mixture is poured into ice-cold water (20 mL), and extracted with dichloromethane (3×50 mL). The combined organics are washed (3×1N HCl, 1×5% NaHCO$_3$), dried (brine, MgSO$_4$) and concentrated in vacuo (<20° C.), with the residue being used directly in the following step.

The crude toluenesulfonate ester from the preceding step is dissolved in toluene (50 mL) and stirred, while trimethylamine (0.8 mmol, 47 mg, 74 µL) is added. The resultant mixture is heated for three hours, or until exhaustion of the toluenesulfonate ester is indicated by HPLC or TLC analysis. The resultant mixture is filtered and the solids washed with toluene. The R-3-hydroxy-4-trimethylammoniumbutyrate ester of abiraterone is purified via reversed-phase HPLC.

Example 3

Gallic Acid Ester of Abiraterone

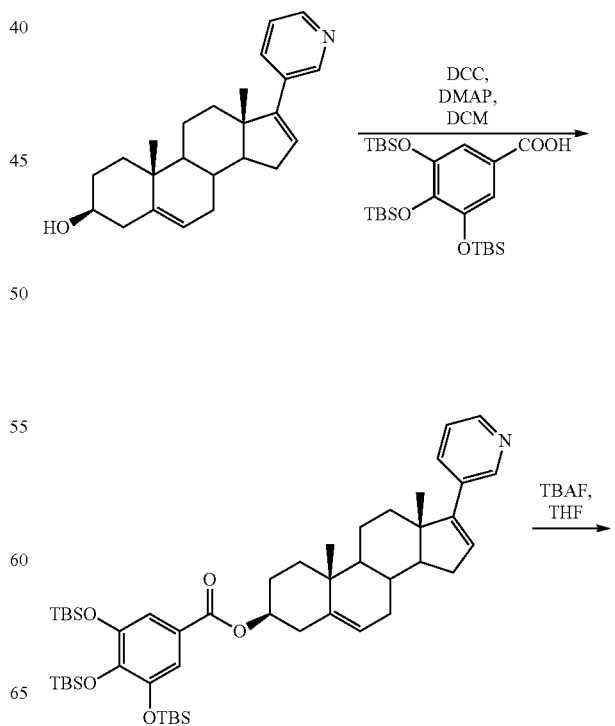

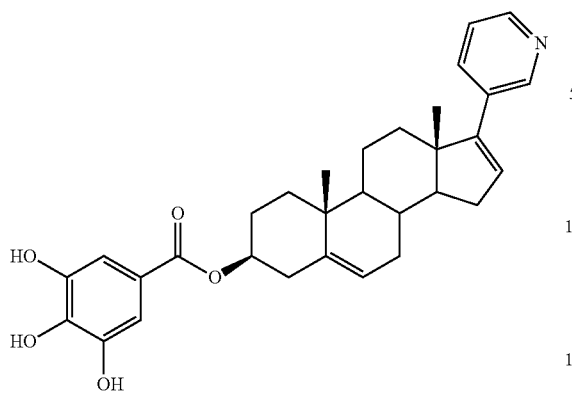

A solution of abiraterone (2 mmol, 747 mg), 3,4,5-tris[(tert-butyl dimethylsilyl)oxy]benzoic acid (2 mmol, 1.026 g), and 4-dimethylaminopyridine (1.0 mmol, 122 mg) in dichloromethane (10 mL) is stirred while dicyclohexylcarbodiimide (2.0 mmol, 412 mg) is added. The resultant suspension is stirred for three hours, and then filtered to remove precipitated dicyclohexylurea. The filtrate is washed with 1N HCl (2×50 mL), and the acid layers are extracted with dichloromethane (1×100 mL). The combined organics are dried (brine, MgSO$_4$), and concentrated in vacuo to afford a solid. The solid is purified by flash column chromatography (silica gel, CHCl$_3$-MeOH) to afford the pure tris-silyl protected ester.

The above prepared ester is dissolved in THF (8 mL) and TBAF is added as a THF solution (1M, 6 mL, 6 mmol) and the resultant solution is stirred for two hours at room temperature. The mixture is poured into half-saturated aqueous sodium chloride and extracted with dichloromethane (2×100 mL). The combined organics are washed (1×1N HCl, 1× water), dried (brine, MgSO$_4$), and concentrated in vacuo to afford the crude gallic ester, which is purified by flash column chromatography (silica gel, CHCl$_3$-MeOH) to afford the pure desired material.

Example 4

Phosphonoacetic Acid Ester of Abiraterone

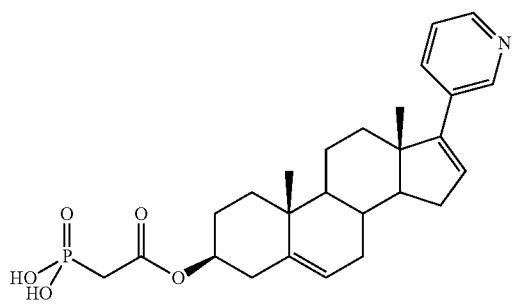

A mixture of phosphonoacetic acid (2 mmol, 280 mg), abiraterone (746 mg, 2 mmol) and 4-dimethylaminopyridine (2.5 eq, 305 mg) in dichloromethane (15 mL) is stirred while EDC-HCl (384 mg, 2.0 mmol) is added. The resultant mixture is stirred for eight hours at room temperature. The mixture is poured into 1N HCl (100 mL) and is extracted with dichloromethane (2×100 mL). The organic layers are combined, dried (brine, MgSO$_4$) and concentrated. The residue is purified by reversed-phase HPLC to afford the desired phosphonoacetic acid ester of abiraterone.

Example 5

Gallic Acid Ester of Compound 5

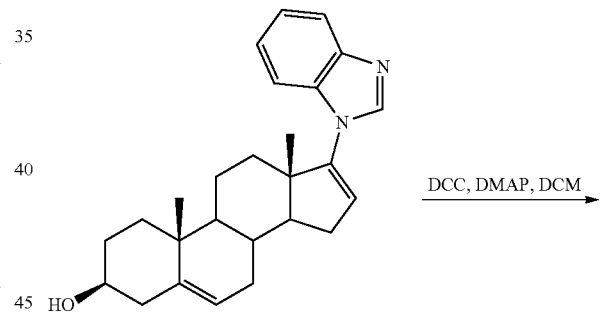

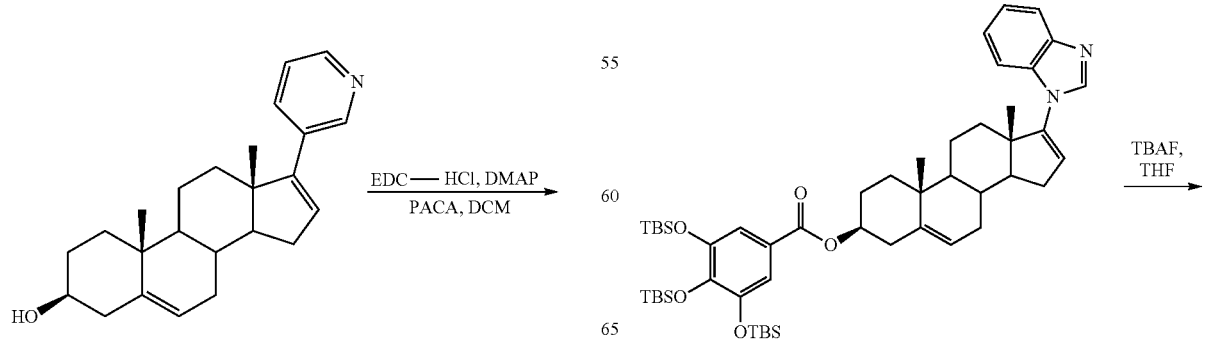

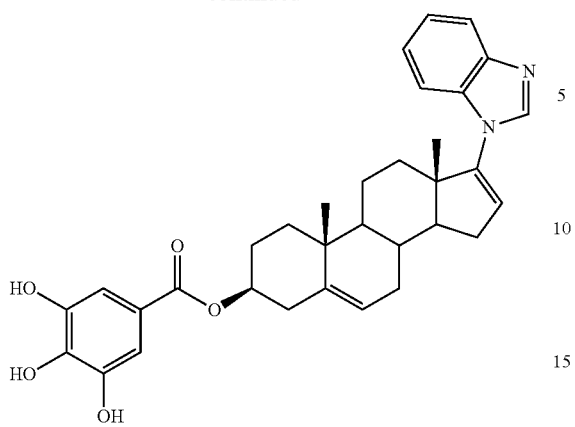

A solution of compound 5 (2 mmol, 777 mg), 3,4,5-tris[(tert-butyl dimethylsilyl)oxy]benzoic acid (2 mmol, 1.026 g) 4-dimethylaminopyridine (1.0 mmol, 122 mg) in dichloromethane (10 mL) is stirred while dicyclohexylcarbodiimide (2.0 mmol, 412 mg) is added. The resultant suspension is stirred for three hours, and then filtered to remove precipitated dicyclohexylurea. The filtrate is washed with 1N HCl (2×50 mL), and the acid layers are extracted with dichloromethane (1×100 mL). The combined organics are dried (brine, MgSO$_4$), and concentrated in vacuo to afford a solid. The solid is purified by flash column chromatography (silica gel, CHCl$_3$-MeOH) to afford the pure tris-silyl protected ester.

The above-prepared ester is dissolved in THF (8 mL) and TBAF is added as a THF solution (1M, 6 mL, 6 mmol) and the resultant solution is stirred for two hours at room temperature. The mixture is poured into half-saturated aqueous sodium chloride and extracted with dichloromethane (2×100 mL). The combined organics are washed (1×1N HCl, 1× water), dried (brine, MgSO$_4$), and concentrated in vacuo to obtain the crude gallic ester, which is purified by flash column chromatography (silica gel, CHCl$_3$-MeOH) to afford the pure desired material.

Example 6

Phosphonoacetic Acid Ester of Compound 5

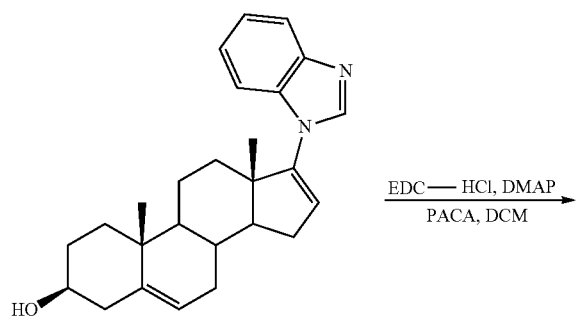

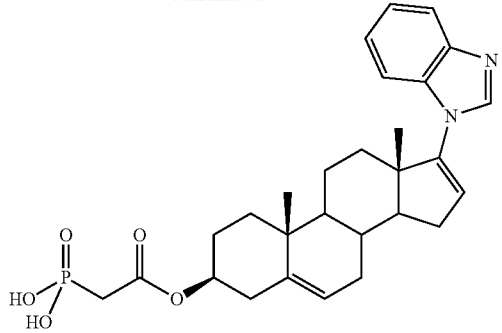

A mixture of phosphonoacetic acid (2 mmol, 280 mg), compound 5 (776 mg, 2 mmol) and 4-dimethylaminopyridine (2.5 eq, 305 mg) in dichloromethane (15 mL) is stirred while EDC-HCl (384 mg, 2.0 mmol) is added. The resultant mixture is stirred for eight hours at room temperature. The mixture is poured into 1N HCl (100 mL) and is extracted with dichloromethane (2×100 mL). The organic layers are combined, dried (brine, MgSO$_4$) and concentrated. The residue is purified by reversed-phase HPLC to afford the desired phosphonoacetic acid ester of compound 5.

What is claimed:

1. A compound of the formula:

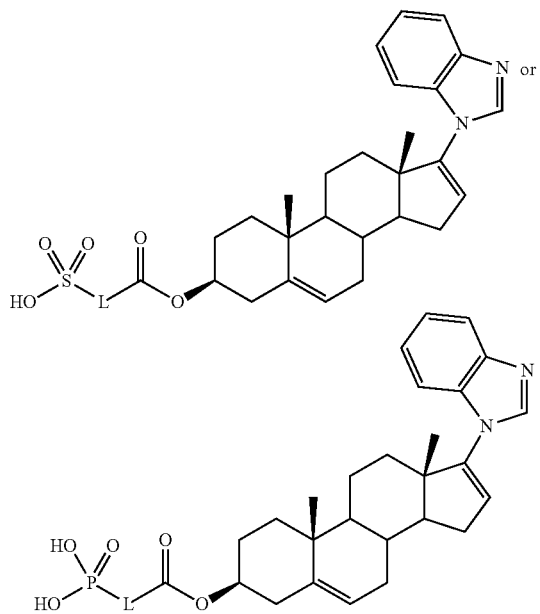

or a pharmaceutically acceptable salt thereof, wherein L is a $C_{1-12}$ alkyl group.

2. The compound of claim 1, or a pharmaceutically acceptable salt thereof, wherein L is a $C_1$ alkyl group.

3. A pharmaceutical composition comprising the compound of claim 1 and a pharmaceutically acceptable carrier.

4. The pharmaceutical composition of claim 3, wherein the composition is an oral dosage form.

5. The pharmaceutical composition of claim 4, wherein the oral dosage form is a tablet, caplet, or capsule.

6. A method of treating prostate cancer or prostate hyperplasia in a subject in need thereof, comprising administering the compound of claim 1 or pharmaceutically acceptable salt thereof.

7. The method of claim 6, for treating androgen-related prostate cancer.

8. The method of claim 6, for treating prostate hyperplasia.

9. The method of claim 6, further comprising administering other cancer treatments selected from an anti-androgen, CYP17 inhibitor, luteinizing hormone-releasing hormone agonist, estrogen, and chemotherapy drug.

* * * * *